(12) United States Patent
Mazzari et al.

(10) Patent No.: US 8,399,262 B2
(45) Date of Patent: Mar. 19, 2013

(54) BIOSENSOR

(76) Inventors: Darrel A. Mazzari, Grafton, WI (US); Martin A. Seitz, Brookfield, WI (US)

( * ) Notice: Subject to any disclaimer, the term of this patent is extended or adjusted under 35 U.S.C. 154(b) by 0 days.

(21) Appl. No.: 13/196,653

(22) Filed: Aug. 2, 2011

(65) Prior Publication Data

US 2012/0244547 A1  Sep. 27, 2012

Related U.S. Application Data

(60) Provisional application No. 61/466,886, filed on Mar. 23, 2011.

(51) Int. Cl.
*G01N 33/551* (2006.01)

(52) U.S. Cl. ... 436/525; 435/7.1; 435/283.1; 435/287.1; 435/287.7; 435/287.8; 435/287.9; 436/518; 436/524; 436/535; 436/806; 422/50; 422/82.01

(58) Field of Classification Search ............ 435/7.1, 435/283.1, 287.1, 287.7, 287.8, 287.9; 436/518, 436/524, 525, 535, 806; 422/50, 82.01
See application file for complete search history.

(56) References Cited

U.S. PATENT DOCUMENTS

| | | | |
|---|---|---|---|
| 5,954,685 A | | 9/1999 | Tierney |
| 6,300,123 B1 * | | 10/2001 | Vadgama et al. ......... 435/287.1 |
| 6,485,905 B2 * | | 11/2002 | Hefti .................... 435/6.11 |
| 7,074,311 B1 | | 7/2006 | Cunningham |
| 7,354,733 B2 * | | 4/2008 | Bukshpan et al. ............. 435/28 |
| 7,413,536 B1 | | 8/2008 | Dower et al. |
| 7,459,303 B2 * | | 12/2008 | Wang et al. ............... 435/287.1 |
| 7,642,053 B2 | | 1/2010 | Gumbrecht et al. |
| 2002/0090649 A1 * | | 7/2002 | Chan et al. .................. 435/7.1 |
| 2004/0118688 A1 * | | 6/2004 | Dumas ..................... 204/548 |
| 2004/0166504 A1 | | 8/2004 | Rossier et al. |
| 2004/0185051 A1 | | 9/2004 | Schmechel et al. |
| 2006/0024813 A1 * | | 2/2006 | Warthoe ................ 435/287.1 |
| 2006/0149337 A1 * | | 7/2006 | John .......................... 607/45 |
| 2007/0037138 A1 * | | 2/2007 | Winther ....................... 435/5 |
| 2008/0039339 A1 | | 2/2008 | Hassibi et al. |
| 2008/0050752 A1 | | 2/2008 | Sun et al. |
| 2008/0139403 A1 | | 6/2008 | Vogel et al. |
| 2008/0176757 A1 | | 7/2008 | Hassibi et al. |
| 2008/0176759 A1 | | 7/2008 | Yamazaki et al. |
| 2008/0182758 A1 | | 7/2008 | Ugolin et al. |
| 2008/0242553 A1 | | 10/2008 | Kayyem |
| 2008/0248966 A1 | | 10/2008 | Hansen et al. |
| 2008/0261825 A1 | | 10/2008 | Brennan et al. |
| 2008/0280776 A1 | | 11/2008 | Bashir et al. |
| 2009/0000957 A1 | | 1/2009 | Dubin et al. |

(Continued)

FOREIGN PATENT DOCUMENTS

| | | |
|---|---|---|
| EP | 1 674 868 | 6/2006 |
| WO | WO-94/23295 | 10/1994 |

(Continued)

OTHER PUBLICATIONS

Darain et al., "Development of an immunosensor for the detection of vitellogenin using impedance spectroscopy", Biosensors and Bioelectronics 19, 2004, pp. 1245-1252.

(Continued)

*Primary Examiner* — Melanie Y Brown
(74) *Attorney, Agent, or Firm* — Foley & Lardner LLP

(57) ABSTRACT

Disclosed herein are biosensors for the detection of airborne biomolecules. The biosensors include a housing, a sensing component, and optionally a sample capture component. The biosensors may utilize a gel-based detection platform.

30 Claims, 26 Drawing Sheets

U.S. PATENT DOCUMENTS

| | | |
|---|---|---|
| 2009/0011946 A1 | 1/2009 | Majumdar et al. |
| 2009/0029870 A1 | 1/2009 | Ward et al. |
| 2009/0036315 A1 | 2/2009 | Labgold et al. |
| 2009/0069194 A1 | 3/2009 | Ramakrishnan |
| 2009/0105087 A1 | 4/2009 | Kahlman et al. |
| 2009/0115434 A1 | 5/2009 | Hirthe et al. |
| 2009/0124513 A1 | 5/2009 | Berg et al. |
| 2009/0181856 A1 | 7/2009 | Van Lankvelt et al. |
| 2009/0181860 A1* | 7/2009 | McKernan et al. ............ 506/16 |
| 2009/0221431 A1 | 9/2009 | Yoo |
| 2010/0041566 A1 | 2/2010 | Zhang et al. |
| 2010/0069253 A1 | 3/2010 | Gindilis |
| 2010/0075340 A1 | 3/2010 | Javanmard et al. |
| 2010/0075865 A1 | 3/2010 | Trau et al. |
| 2010/0113301 A1 | 5/2010 | Remacle et al. |
| 2010/0130725 A1 | 5/2010 | Fang et al. |
| 2010/0137155 A1 | 6/2010 | Akagi et al. |
| 2010/0151580 A1 | 6/2010 | Peppas et al. |
| 2010/0152057 A1 | 6/2010 | Lieber et al. |
| 2010/0184046 A1 | 7/2010 | Klass et al. |
| 2010/0204055 A1 | 8/2010 | Bonner-Ferraby et al. |
| 2010/0222224 A1 | 9/2010 | Suni et al. |
| 2010/0234237 A1 | 9/2010 | Yoo |
| 2010/0240547 A1 | 9/2010 | Greenfield |
| 2012/0116683 A1* | 5/2012 | Potyrailo et al. ................ 702/19 |

FOREIGN PATENT DOCUMENTS

| | | |
|---|---|---|
| WO | WO-2009/117362 | 9/2009 |
| WO | WO-2010/030035 | 3/2010 |
| WO | WO-2010/059687 | 5/2010 |
| WO | WO-2010/062801 | 6/2010 |

OTHER PUBLICATIONS

Rodriguez et al., "Aptamer biosensor for label-free impedance spectroscopy detection of proteins based on recognition-induced switching of the surface charge", Chem. Commun., 2005, pp. 4267-4269.

Sadik et al., "Differential Impedance Spectroscopy for Monitoring Protein Immobilization and Antibody-Antigen Reactions", Analytical Chemistry, vol. 74, No. 13, Jul. 1, 2002, pp. 3142-3150.

Tang et al., "A label-free electrochemical immunoassay for carcinoembryonic antigen (CEA) based on gold nanoparticles (AuNPs) and nonconductive polymer film", Biosensors & Bioelectronics vol. 22, 2007, pp. 1061-1067.

Wang et al., "Application of impedance spectroscopy for monitoring colloid Au-enhanced antibody immobilization and antibody-antigen reactions", Biosensors & Bioelectronics, vol. 19, 2004, pp. 575-582.

Zhu et al., "PAMAM dendrimer-enhanced DNA biosensors based on electrochemical impedance spectroscopy", Analyst, vol. 134, 2009, pp. 860-866.

Chornokur et al., "Impedance-Based Miniaturized Biosensor for Ultrasensitive and Fast Prostate-Specific Antigen Detection", Journal of Sensors, vol. 2011, Article ID 983752, 7 pages.

Ruan et al., "Immunobiosensor Chips for Detectionof *Escherichia coli* 0157:H7 Using Electrochemical Impedance Spectroscopy", Analytic Chemistry, vol. 74, No. 18, Sep. 15, 2002, 7 pages.

Tsai et al., "A novel nanostructured biosensor for the detection of the dust mite antigen Der p2", International Journal of Nanomedicine 2011:6 1201-1208, 8 pages.

International Search Report and Written Opinion for PCT/US2012/029657, mailing date Jan. 2, 2013, 13 pages.

\* cited by examiner $$z_s = z'_s + jz''_s$$
$$= z_{Re} + jz_{Im}$$
$$= R_s + 1/j\omega C_s$$

Four Complex Plane Representations $$Z^* = R_s - j\left(\frac{1}{\omega C_s}\right) \quad = \text{Complex impedance}$$

$$Y^* = G_p + j\omega C_p \quad = \text{Complex admittance}$$

$$C^* = C_p - j\left(\frac{G_p}{\omega}\right) \quad = \text{Complex capacitance}$$

$$M^* = \frac{1}{C_s} + j\omega R_s \quad = \text{Complex modulus}$$

Handheld.

Various antibody attachments

Probe configurations $Z_s = Z'_s + jZ''_s$
$\quad = Z_{Re} + jZ_{Im}$
$\quad = R_s + 1/j\omega C_s$ $Y_p = Y'_p + jY''_p$
$\quad = Y_{Re} + jY_{Im}$
$\quad = G_p + j\omega C_p$ Impedance components EIS plots for bare Au electrode with 0vdc bias and 0.9 vdc bias.

Electrode-Electrolyte interface - Charge distribution-double layer interface

Experimental setup for testing parallel mode electrode.

EIS plots for parallel electrode. Antigen migration through Agrose-Glycerin hydrogel Linear/serial experiment setup with Colloidal Gold / MPTS / Antibody electrode.

Log plots of IgG concentration vs. log change in impedance. All measurements were performed in 10 mM PBS (pH 7.4) Error bars = S.E. (n=4)

Differential Signals (left) IgMab/IgG, (right) IgGab/IgG

BIOSENSOR

CROSS-REFERENCE TO RELATED APPLICATIONS

This application claims the benefit of U.S. Provisional Application No. 61/466,886 filed Mar. 23, 2011.

BACKGROUND

Biosensors are typically used for determining the presence and/or amount of a biological target (analyte) in a sample. In general, a biosensor comprises a bio-component (e.g. an enzyme, nucleic acid, antibody, etc.) which is specific for the biological target (e.g., an analyte such as a substrate or an antigen) and which interacts with the biological target to produce a detectable molecular change. The bio-component is coupled to a transduction system. When the target contacts the bio-component, the molecular change is converted, via the transduction system, to a signal that can be detected by the user. Typical biosensors require a liquid sample and/or a liquid detection platform.

DETAILED DESCRIPTION

Figure 1:
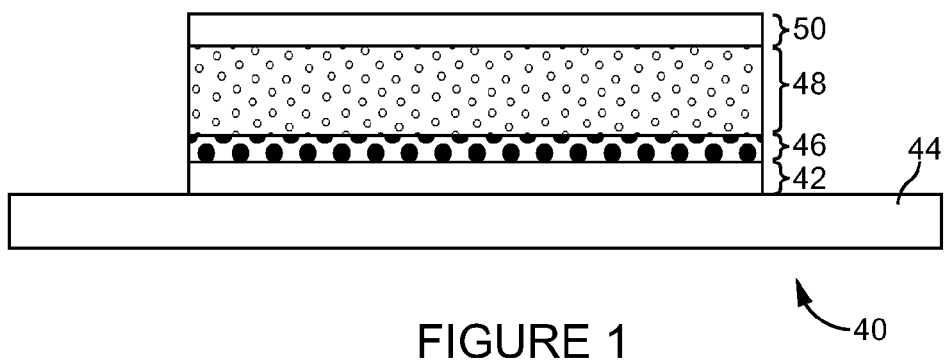
FIG. 1 illustrates one embodiment of a plane parallel sensing component.

Disclosed herein are biosensors for the detection of airborne biomolecules. In some embodiments, portable biosensors are provided. In some embodiments, the biosensors include a housing, a sensing component, and optionally a sample capture component which may contain the sensing component and may further be insertable into the housing. The biosensors may utilize a gel-based detection platform. When a biomolecule of interest contacts the sensing component, a characteristic impedance change is detected, thereby alerting the user to the presence and/or amount of the biomolecule.

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "biomolecule" refers to any organic molecule or structure that is produced by a living organism, including the organism itself, and includes, without limitation, cellular debris, such as cell membrane components, bacterial, fungal and plant cell wall material and components, large polymeric molecules such as proteins, polysaccharides, and nucleic acids as well as small molecules such as primary metabolites, secondary metabolites, and natural products. The terms "biomolecules" and "targets" or "target molecule" are used interchangeably. In some embodiments, biomolecules are indicative of the presence of the organism from which they are derived.

As used herein, the term "fungus" refers to the large group of eukaryotic organisms that includes microorganisms such as yeasts and molds, as well as mushrooms. Mycotoxins can be present in spores and small mold fragments released into the air and can cause coughing, wheezing, runny nose, irritated eyes or throat, skin rash, diarrhea or other types of allergic reactions. Listed below are exemplary molds capable of mycotoxin production.

Molds of the genus *Chaetomium*, such as *Chaetomium Atrobrunneum*. Mycotic infections, referred to as phaeohyphomycosis, due to *Chaetomium* micotoxin, have been documented. Brain abscess, peritonitis, fatal deep mycoses, cutaneous lesions and onychomycosis are examples of diseases or conditions that may develop after exposure. Damage of the myelin sheath can lead to Multiple Sclerosis, Lupus, and even certain forms of cancer. *Chaetomium* sp. can be found on moist substrates containing cellulose, e.g. paper and plant compost.

Molds of the genus *Fusariumi Fusarium* sp. is a hydrophilic mold that thrives in very wet conditions. It can be commonly found in damp wallboard and water reservoirs for humidifiers. While *Fusarium keratitis* can be a serious infection, it is a rare disease.

*Aspergillus* sp. include very toxic *Aspergillus versicolor* and *Aspergillus fumigatus* which tend to colonize continuously damp materials such as damp wallboard and fabrics.

*Penicillium* sp. including *Penicillium notatum* are commonly found in house dust, wallpaper, decaying fabrics, moist clipboards, etc.

*Stachybotrys* sp. mycotoxin is highly toxic. The toxin of this greenish-black, slimy mold found on cellulose products, can be a kidney and liver carcinogen.

Other exemplary fungi or molds include, without limitation those of the genus *Aspergillus*, including as, *Aspergillus niger*, those of the genus *Alternaria*, including *Alternaria tenuis*, those of the genus *Cladosporium* including *Cladosporium herbarum*, those of the genus *Epicoccum* including *Epicoccum nigrum*, those of the genus *Geotrichum* including *Geotrichum candidum*, those of the genus, those of the genus *Phoma* including *Phoma herbarum*, those of the genus *Pullularia* including *Pullularia pullulans*, those of the genus *Rhizopus* including *Rhizopus nigricans*, those of the genus *Rhodotorula* including *Rhodotorula glutinis*.

As used herein the term "pathogen" refers to an infectious agent that causes disease to its host. Exemplary non-limiting pathogens include bacteria, virus, molds, fungus, eukaryotic and prokaryotic microorganisms and parasites, etc.

As used herein, the term "capture molecule" refers to one member of a biological binding pair, the other member being referred to as the "target molecule." Biological binding pairs are molecules that have a specific binding interaction with each other. Exemplary biological binding pairs include, without limitation, antibody-antigen; complementary nucleic acids; enzyme-substrate; aptamer-protein; nucleic acid-protein; hormone-ligand; and receptor-ligand. Either member of the binding pair can be employed as the capture molecule in the disclosed biosensors. In some embodiments, binding pairs include multiple targets and/or multiple capture molecules. For example, a single antigen may be recognized by many different antibodies (e.g., polyclonal antibodies); likewise, a single receptor may recognize more than one ligand. Even though there may be multiple possible targets and/or multiple possible capture molecules, specificity still exists in the various binding pair groups.

As used herein, the term "electrolytic gel" refers to a gel substance which contains ions and can conduct an electric signal. A "gel" may be a colloidal suspension of a solid dispersed in a liquid or a semi-rigid solid which exhibits no flow when in the steady-state. Gels may be mostly liquid by weight, yet they behave like solids due to a three-dimensional cross-linked network within the liquid. In general, the three-dimensional network spans the volume of a liquid medium. This internal network structure may result from physical or chemical bonds as well as crystallites or other junctions that remain intact within the extending fluid.

As used herein the term "sample" is used in a broad sense and refers to a material or medium which include, or is suspected to include, a biomolecule of interest. Exemplary samples include bodily fluids, tissues, gases, air, soil and other material. In some embodiments, the sample comprises an environmental air sample.

Disclosed herein are compositions and methods for detecting biomolecules in a sample or in the environment. In one aspect, a handheld or portable biosensor for the detection of airborne biomolecules is provided. In some embodiments, the biosensor includes a housing, a sensing component and optionally a sample capture component. Generally, the housing is made up of materials and components that are convenient for repeated, hand-held use in the field (e.g., materials and components that are durable, lightweight, portable and easy to use). By way of example, but not by way of limitation, in some embodiments, the housing comprises plastic, and includes a data display screen or graphical user interface (GUI) and a keyboard and/or touch screen. The biosensors disclosed herein also include a sensing component and optionally, a sample capture device which enhances sample capture and may direct the sample to the sensing component.

In some embodiments, the sensing component is fixed in or on the biosensor (e.g., is an essentially permanent component). In other embodiments, the sensing component is removable, and in some embodiments, is configured for a single use. Additionally or alternatively, in some embodiments, a sample capture device is included to enhance sample capture. For example, in some embodiments, a sample capture device includes a vacuum or suction mechanism configured to draw a sample, such as air, into contact with the sensing component. In other embodiments, the sample capture device includes a piezoelectric fan or nanomotor. The forced air sampling system provides for an increased amount of sample to contact the sensing component in a shorter amount of time than passive sample capture.

The sensing component provides a gel-based detection platform that can replace the need for a liquid sample, or a liquid-based detection reaction. In some embodiments, the sensing component includes a capture molecule, an electrolytic gel surrounding the capture molecule, at least two electrodes configured to detect impedance across the electrolytic gel, and an insulating substrate used as a base or platform upon which the capture molecule, electrolytic gel and electrodes may be secured. When a sample (e.g., air) contacts the electrolytic gel of the sensing component, biomolecules present in the sample diffuse through the gel to contact the capture molecules. If the biomolecules and the capture molecules comprise a biological binding pair (e.g., an antigen/antibody binding pair), the biomolecules will bind to the capture molecule causing a change in impedance of the biosensor, which is detectable by an electrical circuit via the electrodes. The impedance change is characteristic of the binding pair, and in some embodiments, the change in impedance is indicated as a display on the data screen or GUI of the housing. Additionally or alternatively, impedance change can be indicated as an auditory signal.

The following figures are provided to aid the reader in understanding various aspects of the disclosed apparatuses and methods; however, the figures and their descriptions are not intended to be limiting.

FIG. 1, illustrates one exemplary embodiment of a sensing component (40), useful in the biosensors disclosed herein.

In FIG. 1, a plane parallel sensing component configuration is shown (40). In the plane parallel configuration, a first conductive electrode (42) is positioned on an insulating substrate (44). Capture molecules (46) are immobilized or disposed on the first electrode (42). An electrolytic gel (48) is positioned to surround the capture molecule layer (46) and to contact the first electrode (42). A second conductive electrode (50) is positioned to contact the electrolytic gel. In this example, the second electrode (50) is an open screen electrode. In use, a sample (e.g., air from the environment) passes through the second electrode screen (50) to contact the gel (48). Biomolecules present in the sample diffuse through the gel (48) and contact the capture molecules (46). If the biomolecules and the capture molecules are members of a biological binding pair, the biomolecules will bind the capture molecules (46). Such binding causes a change in impedance of the biosensor material or layers between electrodes (42) and (50). The impedance is detected by the electrodes (42) and (50) in contact with the gel (48). In some embodiments, the change in impedance is captured or detected or measured, analyzed and transformed by an analysis device and displayed for the user.

Figure 2:
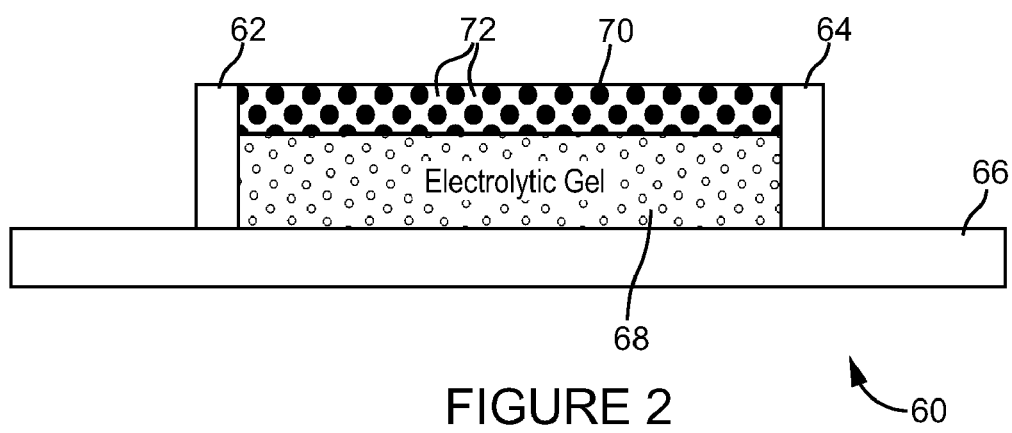
FIG. 2 illustrates one embodiment of a linear sensing component.

FIG. 2 illustrates another exemplary embodiment of a sensing component useful in the biosensors disclosed herein. In FIG. 2, a linear sensing component configuration is shown. In the linear sensing component configuration (60), a first electrode (62) and a second electrode (64) are positioned on an insulating substrate (66), in contact with and sandwiching an electrolytic gel (68). Capture molecules are immobilized on a porous support (70). In this embodiment, the porous support is a string-like medium, which includes capture molecules (72) permeating the support. The porous support is positioned between the first and second electrodes (62) and (64), and is in contact with the electrolytic gel (68). In use, the sample (e.g., air from the environment) and any biomolecules present in the sample contact the porous support (70) and the capture molecules thereon (72). In this embodiment, the porous support (70) is positioned such that no, or very little diffusion time is required for the biomolecules to reach the capture molecules (72). If the biomolecules and the capture molecules are members of a biological binding pair, the biomolecules will bind the capture molecules. Such binding causes a change in impedance detected by the electrodes (62) and (64), in contact with the gel (68). In some embodiments, the change in impedance is captured or detected or measured, analyzed and transformed by an analysis device in the biosensor, and displayed for the user.

Figure 3:
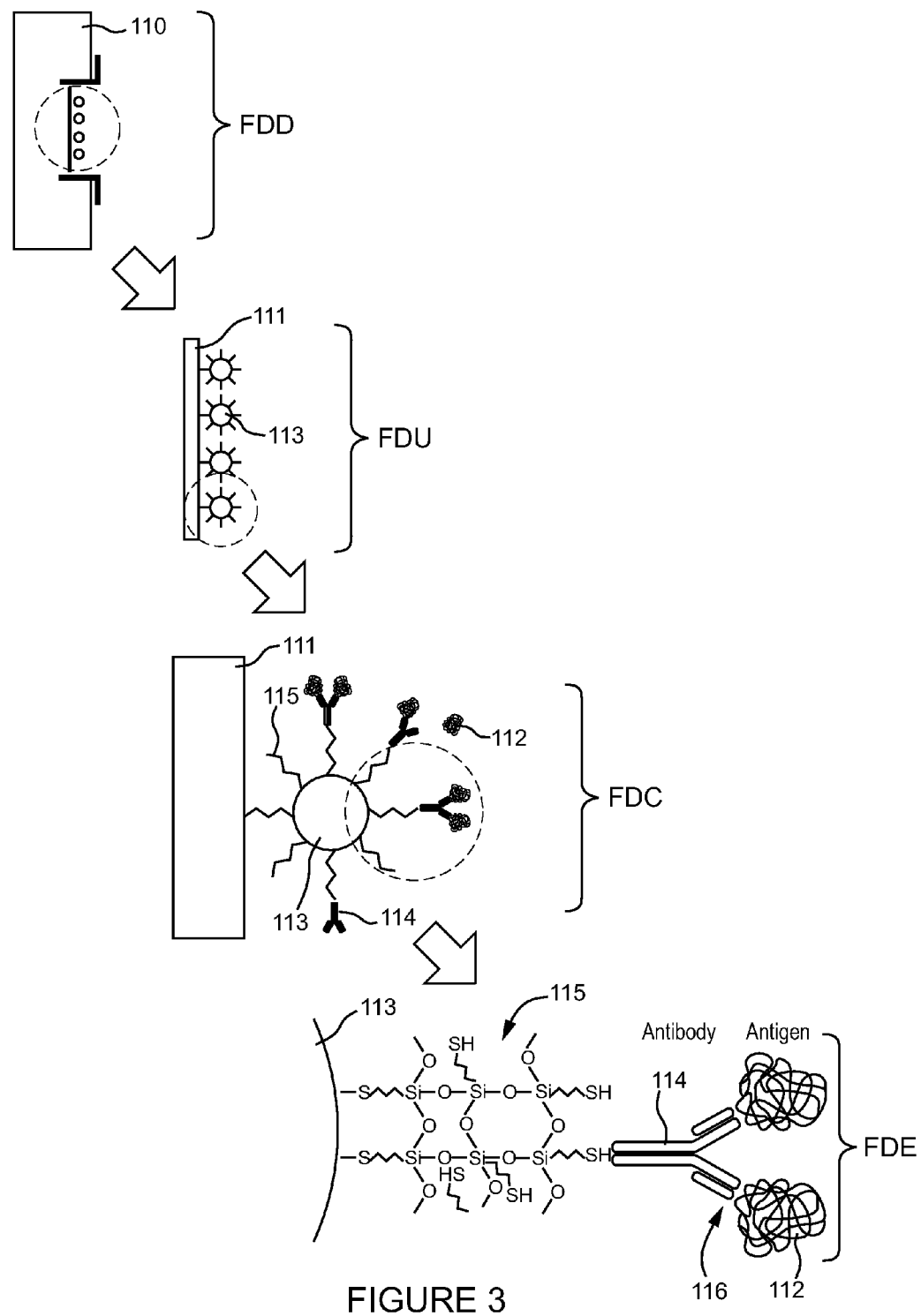
FIG. 3 illustrates one embodiment of a linear (serial) configuration of a sensing component.

FIG. 3 illustrates another example of a sensing component useful in the biosensors disclosed herein.

In the exemplary embodiment of FIG. 3, the FDU (Facilitating Detection Unit or sensing component) is the part of the biosensor that is utilized to detect and determine if an object of interest is present at a location of interest, e.g., in a sample of environmental air. In some embodiments, the object of interest is a biomolecule, such as a biological antigen (115), such as, but not limited to, a protein, bacteria, virus, toxin, or an active, or potentially active, molecular complex, capable of conjugating with an anti-substance (114), e.g. an antibody. In some embodiments, the location of interest is the medium surrounding the FDU. In some embodiments, the medium includes but is not limited to, environmental air. The output of the FDU is the raw data signal or information.

In some embodiments, the FDU raw output is then fed into the FDD (Facilitating Detection Device) that contains the associated electronics and signal processors or other processors that are used to display the results in a user-friendly fashion. Typically, the results are stored in a memory, which may be a removable memory card, RAM, flash memory, etc., which may be stored in the form of a database.

In some embodiments, the FDU is composed of FDCs (Facilitating Detection Components.) In some embodiments, the FDCs are colloidal gold particles (113), each coated with a self assembling monolayer (115) to which antibodies (114) of the antigen of interest are attached. In the serial embodiment, the FDC's are attached and secured to a threadlike component (111) such as, but not limited to, cotton thread, polymer string, carbon, or glass fiber. In some embodiments, the FDC's are selected based upon electrochemical properties and reactions that produce unique and detectable outputs and conditions. In some embodiments, the unique and detectable outputs and conditions are captured and identified through direct measurement, combined into a coherent signal at the FDU, and, then, in some embodiments, are sent to the FDD where the raw data is analyzed with instrumentation, signal processing, and/or data mining.

The use of gold particles between two electrodes enhances the interface effect without doing much to the bulk effect. Every time a charge goes through a gold particle, the charge goes through another interface. The interface effect could be enhanced in alternative ways. For example, instead of a string, a network or matrix of supports, porous or non-porous, could be used to confine the gold nanoparticles. This could be a mesh, such as, but not limited to, silicon, glass, or a polymer, or a sol-gel.

In some embodiments, the FDC contains one or more FDEs (Facilitating Detection Elements) (i.e., the biological recognition element or capture molecule). In some embodiments, the FDEs comprises the precise methodology used to detect the target molecule, e.g., an antigen. For example, in some embodiments, it is the bonding of the "lock and key" association (116) of the antigen and its associated antibody.

In some embodiments, the "lock and key" interaction between molecules in order to form bonded conjugates (binding pairs) relies on the shape of each molecule. In some embodiments, the binding is covalent. In some embodiments, the binding is ionic. For example, in order for antibodies to conjugate with antigens specific to them, the antibodies and antigens are provided in a medium that allows movement (e.g., to align the target and capture molecules, and move them together) e.g., to insert the "key" in the "lock." Typically, the medium does not alter the shape of the molecules by breaking or bending bonds, modifying secondary or tertiary structure, etc.

Some liquids can fulfill these conditions and facilitate the binding of capture and target molecules; typically, however, such a medium does not include dry air. Typically, in dry air, the capture molecules and/or the target molecules would eventually dry out and may undergo conformational change. Therefore, in embodiments disclosed herein, a gel may be used as the capture molecule medium.

A gel may be a colloidal suspension of a solid dispersed in a liquid or a semi-rigid solid which exhibits no flow when in the steady-state. Though gels may be mostly liquid by weight, they may behave like solids due to a three-dimensional cross-linked network within the liquid. The internal network structure results from physical or chemical bonds, crystallites or other junctions that remain intact within the extending liquid. In some embodiments, the target molecules, e.g., antigens that come in contact with the surface of the gel are captured ("stick") at that point and, then, defuse down into the gel.

The sensing components are not limited by the method used to link the capture molecules to the sensing component. In general, the capture molecules are linked to or disposed on a support which is provided as a part of the sensing component. In some embodiments, supports include solid supports such as an insulating substrate (e.g., flat or string-like), an electrode surface, a particle (e.g., a colloidal gold particle, a synthetic polymer, etc.). Additionally or alternatively, in some embodiments, relatively porous supports, such as a thread-like material, a sponge-like material or a hydrogel are used. Attaching, linking or trapping the capture molecules with the support prohibits or limits diffusion of the molecules away from the support.

Numerous methods and chemistries for linking a capture molecule, such as an antibody, a nucleic acid or a polypeptide, to a solid support may be used, and exemplary methods described herein are provided to aid the reader, but are not intended to be limiting. One technique for the immobilization of capture molecules on the surface of a solid support, such as an electrode or a particle, is to functionalize the support, e.g., to configure the support to secure the capture molecules. For example, in some embodiments, a support is coated with a functionalizing agent that serves to secure or immobilize the capture molecules, and in some embodiments, capture molecules are secured directly or indirectly to the functionalizing agent. Additionally or alternatively, in some embodiments, capture molecules are coated onto a first solid support, such as colloidal gold beads, and the first solid support, including the capture molecules, is secured to a second solid support, such as an electrode or other substrate. Either or both of the supports may be functionalized to enhance the linkage of the solid support and/or the capture molecules, and/or to enhance the number of capture molecules present in a given area or in a given volume. Microbeads, such as, for example, gold, carbon, glass, or polymers, coated with antibodies may be used to amplify the detection signals. Additionally or alternatively, in some embodiments, interdigitated electrodes can increase surface area and electric fields in small areas.

As discussed above, functionalizing agents may be used. For example, in some embodiments, capture molecules are secured to a support that includes self-assembled monolayers ("SAM's"). Thus, in some embodiments, the functionalizing agent is a self-assembling monolayer sol-gel such as, but not limited to, methacryloxypropyltrimethoxysilane (MTPS). MPTS is a bifunctional molecule that contains both thiol and silane functional groups. The thiol groups are the binding sites for the covalent attachment of MPTS to gold surfaces. The sulfur-gold bond has several advantages. The sulfur-gold bond is a strong covalent bond with a high bond enthalpy of 418±25 kJ/mol, and this bond has been measured at a force of 1.4±0.3 nN at loading-rates of 10 nN/sec. Bonds between biomolecules are generally weaker.

To amplify the signal, colloidal gold may be used as the ion conductor replacement to the redox mediator. Each colloidal gold nanoparticle in the linear (or serial) embodiment is covered with a covalently attached, self assembling monolayer of solgel MPTS, as one might imagine grass on a basketball. In another embodiment, they are covalently attached with a theoretical MPTS molecule length of 0.77 nm to the gold base electrode.

In other embodiments, the functionalizing agent is an alkanethiol or alkylamine. Charge transport through alkane monolayers on gold measured as a function of molecule length in a controlled ambient using a metal/molecule/nanoparticle bridge structure shows that the current through molecules with an amine/gold junction is observed to be more than a factor of 10 larger than that measured in similar molecules with thiol/gold linkages. For example, in some embodiments, monolayers are formed via alkanethiol-gold linkage and related linkages between carboxylates and phosphonates and metal oxide surfaces, for example metal electrode surfaces, such as Mg.

In other embodiments, the antibody of interest can be attached to a different antibody, which has, in turn, been bound to an electrode or colloidal gold, or monolayer attached to a metal electrode. In other embodiments, antibodies can be attached to microbeads.

Capture molecules can also be provided to a sensing component by providing a porous support permeated with the capture molecules. In some embodiments, the capture molecules are secured to, linked to or associated with a porous support, such as for example, a relatively porous sponge-like material, a relatively porous string-like material, or a hydrogel. In some embodiments, isoelectric points of the gel material are in the range of 4.5 to 5.0. Additionally or alternatively, in some embodiments, capture molecules in the range of, but not limited to, 20 to 40 nm are used. Sodium dodecyl sulphate-polyacrylamide gel electrophoresis (SDS-PAGE) analysis can be used for molecular weight distribution. Additionally or alternatively, in some embodiments, no chemical modifications or covalent linkages are employed and the capture molecules remain associated with the porous support for sufficient time and at sufficient concentration for a detection reaction and the subsequent change in impedance to occur.

In some embodiments, a porous thread-like material is used as a support. In some embodiments, the thread-like material is saturated with a solution/suspension of capture molecules, with the capture molecules permeating the pores of the thread-like material that is positioned on the surface of an electrolytic, or non-electrolytic gel. In some embodiments, a solid, insulating, string-like material, as, for example, polymer "fishing line", is utilized to immobilize the capture molecules by covalent or other attachment.

In some embodiments, insulating substrates are used in the sensing components. Insulating substrates provide not only a support platform upon which to position various sensor components, but also serve to insulate or isolate the electrical activity occurring within the gel from outside interference. In addition, insulating substrates, also non-ionic surfactants, such as Tween 20, may be used to prevent nonspecific adsorption. The nonspecific adsorption can be totally inhibited by hydrophobic interactions of IgG on methyl ended groups, whereas the surfactant encourages electrostatic/hydrogen bonding interactions with the exposed carboxylic groups as the concentration IgG is determined by the ratio of COOH/CH3-terminated thiols with SAM's (Wang 2006.) Insulating substrates include, without limitation pH glass, silver halide, silver iodide membranes, valinomycin and bis-crown ether based potassium sensitive electrodes.

In some embodiments, the sensing components disclosed herein include at least two electrodes, configured and positioned to detect changes in impedance in an electrolytic gel which is in contact with the capture molecules. These binding reactions will shape the impedance spectrum recorded when a small electrical signal (e.g., 5-10 mVac) is applied to the interface. By tracking the data before and after a bioconjugal event, in one case the union of an antibody and its associated specific antigen, a pattern, like a fingerprint, can be defined and used to identify a similar event occurrence of the same type. Electrodes are used in biomedical applications for both making measurements of biological events and also to deliver current to biological entities. In some embodiments, measurements, for the sake of accuracy and pseudo-linearity, involve low current density—and small size—to introduce the least amount of perturbation which could alter the operation of the process to be measured.

The size, shape and composition of each electrode can vary depending on the configuration of the gel and capture molecule components. For example, in some embodiments (e.g., in plane parallel embodiments such as that shown in FIG. 1), an electrode includes a conductive side and a functionalized side. In some embodiments, the conductive side is gold plated and is positioned to be facing, and in contact with, the insulating substrate. The functionalized side of the electrode is configured to secure the capture molecules. For example, in some embodiments, the functionalized side is coated with a functionalizing agent that serves to secure or immobilize the capture molecules. In some embodiments, capture molecules are immobilized directly on the functionalizing agent. Additionally or alternatively, in some embodiments, capture molecules are coated onto a solid support, such as, for example, colloidal gold beads or glassy carbon, and the solid support including the capture molecules is secured to the functionalized side of the electrode. In some embodiments, the functionalizing agent is a self-assembling monolayer sol-gel such as, but not limited to, methacryloxypropyltrimethoxysilane (MTPS). For example, in one non-limiting embodiment, nucleic acid probes are used with electropolymerized polypyrrole (PPy) film onto a carboxylic group-functionalized multi-walled carbon nanotube modified electrode used, for example, in DNA detection. In some embodiments, the electrode can be glassy carbon.

In some embodiments, an electrode is in the form of a metallic screen or mesh. As shown in FIG. 1, even when such an electrode is positioned directly on the gel layer, the electrode does not prevent the sample (or biomolecules in the sample) from contacting the gel layer.

A method can be used to control the sensitivity of the biosensor. An electrical bias DC voltage, ideally valued to keep the pH of the gel near the isoelectric point (pI), or IEP (the pH at which a particular molecule or surface carries no net electrical charge) is introduced. By varying the voltage, a method is provided to both turn on the biosensor, and turn it off to repel non-specific antigens; in effect, to clear the binding sites. This could also be used for regeneration (by unbinding the binding sites) and reuse. A −25 mvdc to −2 vdc for 30 seconds can be applied to change the pH of the antibody/antigen conjugates to change the pH from a nominal pH to a pH 3.5 which is sufficient to dissociate antibody/antigen conjugates without producing artifactual increases, or inactivating future antibody binding. The negative charge will also repel antigens to clean the antibodies on the electrodes.

In some embodiments, by adjusting the DC voltage bias across the sensor, the pH of the gel can be varied. If the pH is varied significantly from the isoelectric point, the capture molecule, e.g., an antibody, may not conjugate or bind with the target, e.g., an antigen, and may even release target molecules already bound. This will uncover the binding sites or "clean" them, allowing conjugation with new antigens when the DC voltage bias, and thusly pH, is returned to the operating level. A DC bias voltage can also be used to adjust for temperature variations, since temperature can also affect binding (conjugation.) A temperature sensor is utilized in the attached FDD or handheld processor unit to sense temperature, and a circuit may be configured to adjust the dc voltage bias to increase or decrease based on changes in temperature, for example with reference to parameters prestored in memory (e.g., in the form of a look-up table). The temperature sensor would sense the temperature of the gel surrounding the antibody functionalized gold or colloidal gold electrode.

Figure 14:
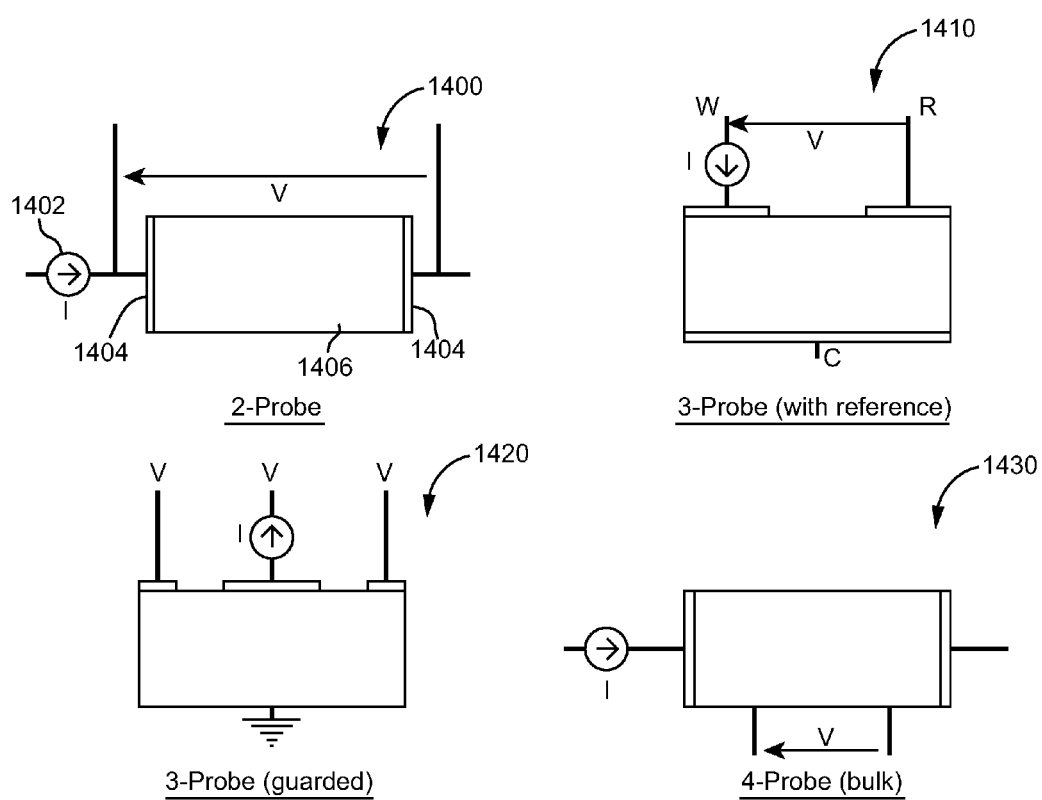
FIG. 14 shows various electrode configurations.

Referring now to FIG. 14, several alternative embodiments of probe or electrode configurations for use with the biosensor assembly are shown. In some embodiments, a two-probe system (probe 1400) can be used if the medium characteristics are also to be contributing to the measurements, or are negligible and can be ignored. Probe 1400 is a two probe configuration having a current source 1402 coupled to one probe 1404. A voltage measurement is taken across the probes coupled to electrodes on opposite sides of the biosensor material 1404 by a processing circuit to measure impedance. Probe 1410 is a 3 probe EIS (electrochemical impedance spectroscopy) measurement system cell containing a platinum wire counter electrode C, a Ag—AgCl reference electrode R, and a working electrode W with a modified Au base. Probe 1420 is a three-probe (guarded) system. Probe 1430 is a four-probe (bulk) system. Although IS (impedance spectroscopy) measurements on solids or dielectric liquids usually involve cells with two identical plane, parallel electrodes, the situation can be complicated for measurements on liquid electrolytes. In one embodiment, one or more small working electrodes, a very small reference electrode, and a large counter electrode may be used. Such an arrangement ensures that everything of interest (related to immittance) happens at or near the working electrode(s). Because the kinetics of electrode reactions often depend strongly on the static (dc) potential difference between the working electrode and the bulk, or, equivalently, the working electrode and the reference electrode, a potentiostat is used to fix this potential difference to a known and controllable value. Utilizing a two-probe system such as probe 1400 may be advantageous in an embodiment using a simultaneous application of both ac and dc signals. In a serial (linear) embodiment, the bulk impedance is not of concern, since the distance to the surface of the gel is very small, and significant reactions take place in the Stern layer. In each of these embodiments, the bias voltage technique in the previous paragraphs can be applied.

The biosensors disclosed herein are not limited by either the type or identity of the capture molecule or the biomolecule target, since the binding pair (i.e., capture molecule and target biomolecule) is selected based on the intended function of the biosensor. For example, in different embodiments, the biosensor may be configured to detect the presence of a biological contaminant, such as a fungus, bacterium or virus in a food preparation environment, a hospital environment, a combat or military environment, a work, a home, or a public gathering environment. By way of example, but not by way of limitation, a biosensor is configured to detect the presence of a household mold such as *Stachybotrys chartarum* (*Stachybotrys atra*). Antibodies specific for the mold of interest are immobilized on the sensing component. An air sample to be tested is then contacted with the sensing component, and if a characteristic change in impedance is detected (e.g., a change in impedance indicative of the binding of the biomolecule and the capture molecule and/or an impedance change that matches the impedance parameters in the memory of an analysis device), the presence of the mold may be confirmed by the processing circuit of the device. In other embodiments, the biosensor is configured to detect the presence of a bacteria or a virus in the environment, and the sensing component includes an antibody specific for the bacteria or the virus to be detected. Viral or bacterial antigens may be present in the air, for example, in proximity to an infected subject, a contaminated water or food source, or in the air generally. If the air sample causes a characteristic change in impedance, the presence of the virus or the bacteria may be confirmed by the processing circuit of the device.

As noted previously, the biosensors disclosed herein are not limited to antibody-antigen binding pairs. For example, in some embodiments, the capture molecule is a nucleic acid, and the complementary nucleic acid is the biomolecule to be detected. Additionally or alternatively, the capture molecule is an enzyme, and a substrate is the biomolecule to be detected. Additionally or alternatively, the capture molecule is an aptamer, and a polypeptide aptamer target is the biomolecule to be detected. In some embodiments, the identity of the capture molecule and biomolecule target is reversed, and the capture molecule is an antigen, a nucleic acid, a substrate, and/or the polypeptide aptamer target, while the target molecule is an antibody, nucleic acid, enzyme and/or aptamer.

The biosensors disclosed herein can be used to detect any number of different biomolecules. In some embodiments, the biomolecules to be detected are derived from one or more of plants, fungi (including molds), bacteria, yeasts, viruses and eukaryotic and prokaryotic microorganisms and parasites. Non-limiting examples of such organisms include, but are not limited to, eukaryotic protozoa of the genus *Giardia*, protozoan parasites in the phylum Apicomplexa such as *Cryptosporidium*, and bacteria such as *Bacillus anthracis, Salmonella* sp., *Staphylococcus aureus, Vibrio, Listeria monocytogenes, Clostridium botulinum, Escherichia coli* (*E. coli*), *Mycobacterium tuberculosis* and *Legionella pneumophila* which causes legionellosis (i.e. Legionnaires' disease and Pontiac fever.) Exemplary non-limiting molds include *Chaetomium atrobrunneum, Fusarium, Aspergillus versicolor* and *Aspergillus fumigatus, Penicillium*, and *Stachybotrys*.

The methods and compositions disclosed herein are not limited by the biomolecule to be detected. For example, in some embodiments, biomolecules include one or more of a cell wall membrane or a portion or a cell wall or cell membrane, a protein, a receptor, a nucleic acid, lipid, carbohydrate, or combinations thereof. Additionally or alternatively, in other embodiments, the biomolecule includes a virus, a viral protein, or a viral nucleic acid. Additionally or alternatively, in still other embodiments, the biomolecule includes a plant component, such as pollen, or a portion of a plant component.

Method of preparing and isolating antibodies, both monoclonal and polyclonal, polypeptides and nucleic acids useful as capture molecules are well known in the art (see e.g., Sambrook et al., *Molecular Cloning, A Laboratory Manual*, Cold Spring Harbor Press (eds.)).

The biosensors disclosed herein are not limited to the detection of a single biomolecule. In some embodiments, multiple biomolecules are detected using a single biosensor. For example, in some embodiments, a single sensing component includes capture molecules from different binding pairs, and allows for the detection of more than one biomolecule. In some embodiments, a single sensing component includes two, three, four, five, six, seven, eight, nine, ten or more different types of capture molecules and is capable of detecting two, three, four, five, six, seven, eight, nine, ten or more different types of biomolecules. For example, in some embodiments, biosensors and the sensing components are configured to detect multiple different genera or species of fungi, multiple bacterial strains, multiple viral strains, multiple pollen strains, etc.

Additionally or alternatively, in some embodiments, a single biosensor is configured to read different sensing components, where the different sensing components are configured to detect a single specific target molecule.

Additionally or alternatively, in some embodiments, multiple biosensors, each with different specific antibodies immobilized thereon, and positioned so as to interact with a same sample, can be sequentially electrically scanned and analyzed for impedance data. This configuration reduces chances of false positives in the instance that the specific antigen of interest has multiple, but non-identical epitopes (sites on the surface of an antigen molecule to which an antibody attaches itself.) This configuration may also allow simultaneous detection of multiple different antigens. The EIS signals from the multiple biosensors may be multiplexed to simplify the circuitry.

In another embodiment, multiple sensors are deployed on a single sensor head, housing, substrate or board, the multiple sensors being controlled by multiplexing the EIS signals generated by a processing circuit so that each sensor may be measured sequentially. Alternatively, the sensors may be read in parallel with suitable circuitry. A first subset of the sensors (e.g., one sensor, perhaps two or more sensors for redundancy) comprise a specific antidogy to the antigen of interested attached to the MPTS. A second subset of the sensors (or perhaps all remaining sensors on the sensor head) comprise a different antibody or a blocking agent (e.g., bovine serum albumin or BSA) attached to the MPTS ends. The processing circuit may be configured to determine a differential signal by comparing the sensor output signal of the first subset of the sensors to the second subset of the sensors. The processing circuit may be configured to determine the presence, absence, or a quantity of the antigen of interest based on the differential signal. In this embodiment, the differential signal may filter out background noise, for example due to non-specific antigens. If all sensors in the first and second sub sets produce a similar EIS output signal, then the processing circuit would determine that no specific antigens are present. If a significant number of the sensors in the first subset produced an identifiable output (e.g., a shift in signal magnitude greater than a predetermined magnitude), and the sensors in the second subset did not respond in the same or similar manner, then the processing circuit may determine that the specific antigen is present.

The electrolytic gel may be any gel which provides or includes ions and conducts an electric signal. In one exemplary non-limiting embodiment, the electrolytic gel includes glycerin, distilled water and agarose; optionally, a redox probe (such as potassium ferricyanide/ferrocyanide, $K_3[Fe(CN)_6]/K_4[Fe(CN)_6]$) may be added to facilitate ion transfer for electrical current conduction. Additionally or alternatively, the electrolytic gel may include acrylamide, polyacrylamide, or other crosslinked polymers As described above, the gel essentially surrounds the capture molecules and in some embodiments, serves not only to conduct an electrical signal between the electrodes for impedance measurement, but also to protect the capture molecules and preserve or maintain their functional conformation. In general, the gel is easily applied in the liquid phase, and in some embodiments the gel is contacted with the capture molecules at a temperature that will not denature or alter the effectiveness of the capture molecules.

In some embodiments, the concentrations of the ingredients which also allow the antibodies to retain their bioactivity are determined and optimized, and the electrical characteristics of the gel to be used are also evaluated.

In one non-limiting embodiment, a hydrogel was made from 0.3 grams of agarose (Sigma A9539) added to 30 ml of distilled $H_2O$. This was heated in a 1000 watt microwave oven for 40 seconds. Then, 10 ml glycerin was added and the solution was boiled in the microwave for 30-40 more seconds, until clear. This hydrogel is termed Glycerin-$H_2O$-Agarose gel, or "GHA" gel.

In alternative embodiments, the glycerin/water ratio may be greater than about 1:3, between about 1:3 and about 1:1, less than about 1:1, or other ratios.

In some embodiments, impedance data derived from the sensing component is captured, analyzed, converted and/or displayed, via an analysis device, for the user. One non-limiting example of a biosensor, including an analysis device, is provided in detail below.

One or more of Nyquist, Bode (FIG. 9), and cyclic voltammetry (FIG. 10) plots may be generated by the electrical circuit to provide the informative output. Prior studies have detected carcinomic antigens (Tang, et al., *Biosensors & Bioelectronics*, 22(6):1061-1067, 2007), DNA hybridizations (Zhu, et al., *Analyst*. 134(5):860-6, 2009), and antibody-antigen reactions (Wang, et al., *Biosensors & Bioelectronics*, 19:575-582, 2004).

Figure 4:
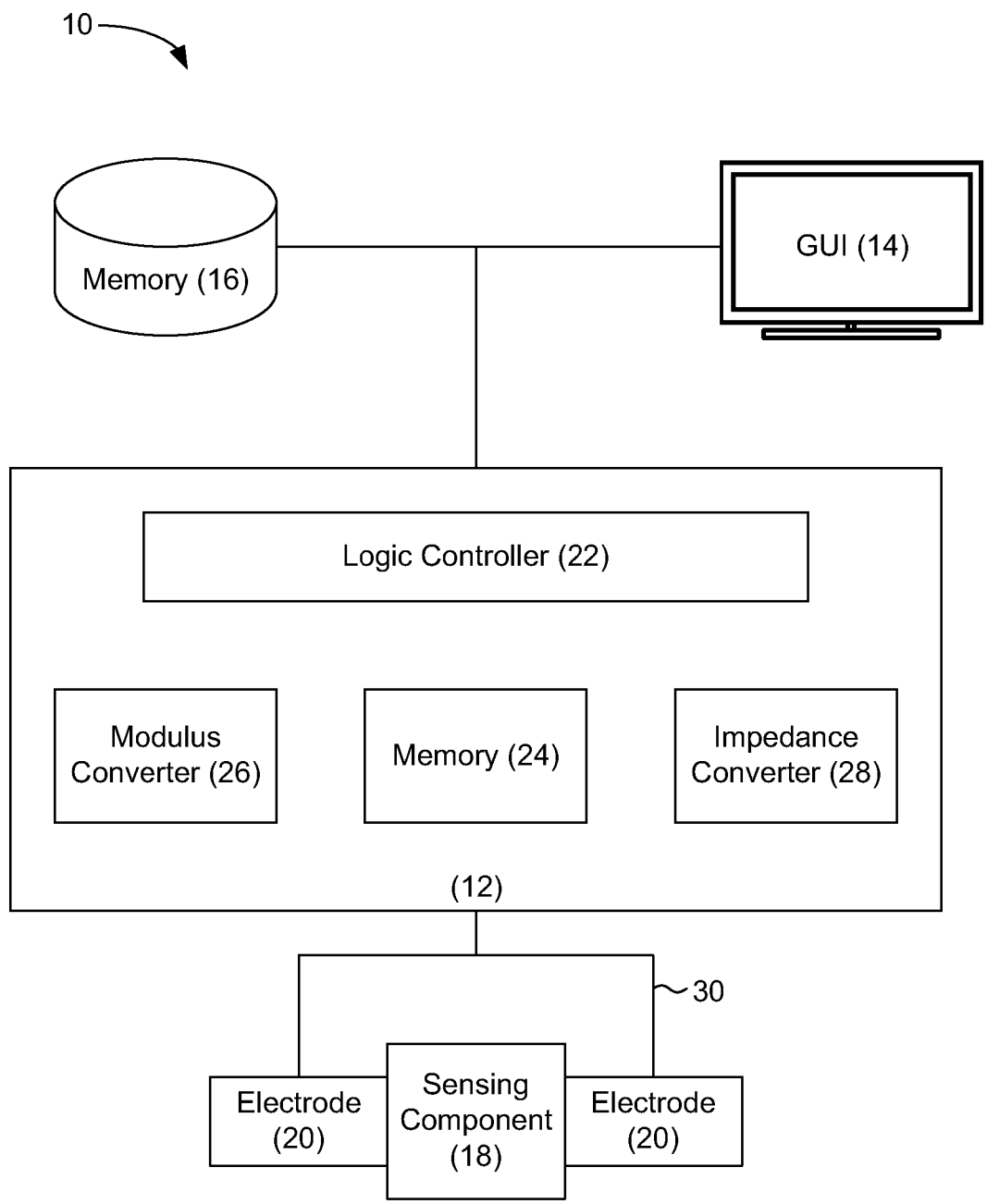
FIG. 4 is a block diagram of a biosensor in accordance with at least one embodiment disclosed herein.
Figure 7:
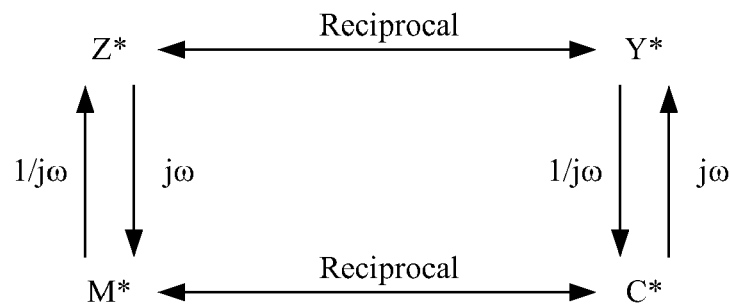
FIG. 7 is a complex plane representation mathematical sequence.

Referring to FIG. 4, an illustrative example of the biosensor assembly 10 in accordance with one embodiment includes an analysis device or impedance measurement circuit (12), a graphical user interface (GUI) (14) and a memory storage device (16). The analysis device (12) includes a logic controller (22), a memory storage device (24), a modulus converter (26) and an impedance converter (28). The sensing component (18) may, be separately connected to biosensor assembly 10, and can alternatively be integrated within the analysis device 12. Sensing component (18) may be a discrete separatable or insertable structure or it may be part of an assembly. Electrodes (20) on the sensing component (18) provide an input signal to the sensing component. An excitation voltage ($V_{(f)}$) is applied to the electrodes, and a response current ($I_{(f)}$) over a range of frequencies is measured and provided to the analyzer (12) via impedance circuit (30). With a slightly basic gel environment of pH 7.4, the nominal dc potential offset is between 0.01 and 1 vdc, and $V_{(f)}$ is between 3 and 20 Vac, with about 10 Vac being preferred. The ac frequency range for the electrochemical impedance spectroscopy (EIS) measurements may be from about 0.1 Hz to 1 MHz with an exemplary range for field use of about 0.1 Hz to 10 KHz in the interest of time. The impedance data is analyzed and converted by the impedance converter (28), and then transferred to the modulus converter (26). The impedance data includes $Z_{real}$, $Z_{imaginary}$, and frequency. The modulus data includes $M_{real}$, $M_{imaginary}$, and frequency. The facilitating detection device (FDD) or handheld device measures impedance, the impedance is converted to digital form with the impedance converter, and then the digital form is mathematically converted to modulus and stored to be used in computing the key parameters for detection (see FIG. 7). In an embodiment in which the FDD is handheld device, the device may be powered by a battery. The logic controller (22) operates the modulus converter (26) and impedance converter (28) to store the respective data, including the impedance measurements (impedance parameters) within memory (24). The logic controller performs a computer readable function, which is accessed from memory (24), that performs an impedance spectroscopy analysis method (see e.g., FIG. 5) and provides a readout to the GUI (14). Additionally or alternatively, in some embodiments, an external memory device (16) is provided, e.g., to save impedance data. For example, the external memory device (16) can be a relational database or a computer memory module. The readout provided via display signals and/or audio signals to GUI may include information regarding the presence and/or amount of the biomolecule(s) of interest.

Figure 6:
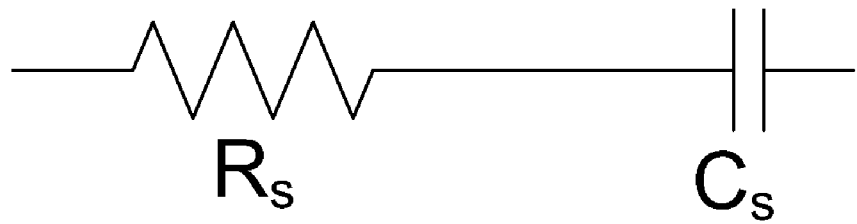
FIG. 6 is a measured form calculation sequence.
Figure 15:
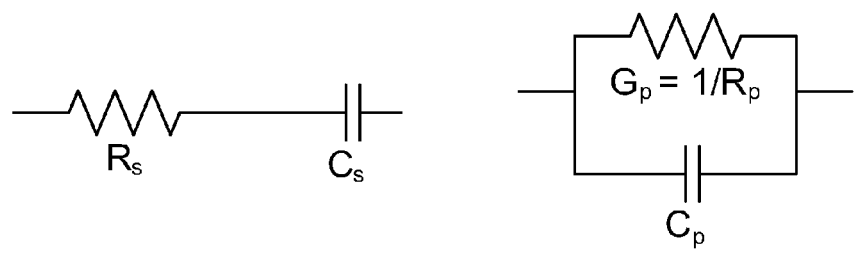
FIG. 15 shows impedance components.

Referring now to FIG. 6, generally, the impedance at a given frequency, ω, contains two components, a real component and an imaginary component. Impedance can be represented using the following expression:

$$Z_s = Z_s' + jZ_s''$$

where $Z_s$ is the impedance, $Z_s'$ is the real component of the impedance, or the resistance, and $Z_s''$ is the imaginary component of the impedance, or the reactance. The impedance can also be represented as a function of the frequency ω according to the following expression:

$$Z^*(\omega) = R_s - j(1/(\omega C_s))$$

where $R_s$ is the resistance measured across the electrodes and $(1/(\omega C_s))$ is the capacitive reactance. As described and illustrated in FIG. 7, the complex impedance can be converted into one or more alternative complex plane representations. For example, complex admittance is the reciprocal of complex impedance and provides a measure of the allowance (e.g., as opposed to the opposition) of alternating current. FIG. 15 illustrates various corresponding expressions for representing data as a complex impedance (left column of FIG. 15) and complex admittance (right column of FIG. 15), according to an exemplary embodiment.

Another representation, a complex modulus representation, is obtained by multiplying the complex impedance by "jω" and may be represented as follows:

$$M^* = 1/C_s + j\omega R_s$$

Figure 8:
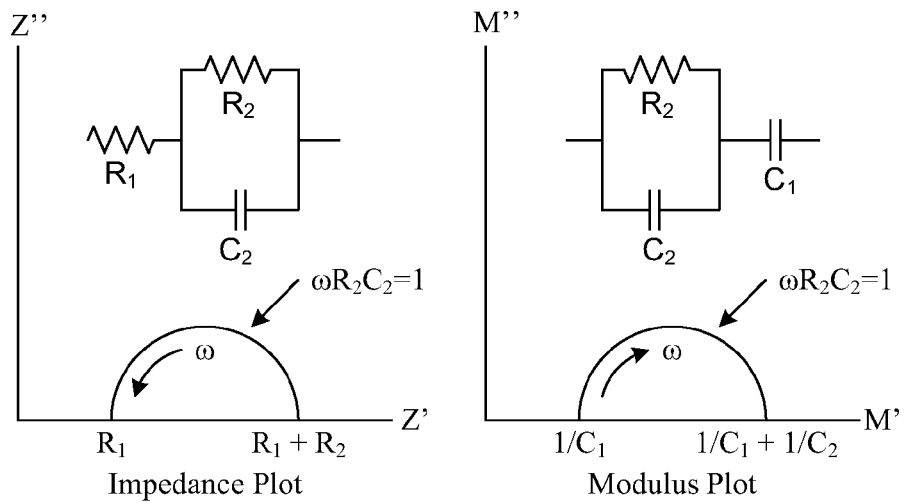
FIG. 8 is an impedance and modulus plot sequence.

FIG. 8 provides a graphical representation of the relationship between the complex impedance representation and the complex modulus representation. In the leftmost plot, or impedance plot, the Z' axis represents the real component of the complex impedance (i.e., $R_s$) and the Z" axis represents the imaginary component of the complex impedance (i.e., $(1/(\omega C_s))$). The circuit shown above the impedance plot is a simple circuit that may be used to represent the complex impedance expression according to an exemplary embodiment. In the rightmost plot, or modulus plot, M' represents the real component of the complex modulus (i.e., $1/C_s$) and M" represents the imaginary component of the complex modulus (i.e., $\omega R_s$). The circuit above the modulus plot is a simple circuit that may be used to represent the complex modulus expression according to an exemplary embodiment. In each plot, the arrow next to the frequency ω indicates a direction of movement along the curve as the frequency ω is increased. In some embodiments, a modulus converter (e.g., modulus converter 26) may be configured to convert a representation to or from a complex modulus representation (e.g., from a complex impedance representation to a complex modulus representation), and an impedance converter (e.g., impedance converter 28) may be configured to convert a representation to or from a complex impedance representation (e.g., from a complex modulus representation to a complex impedance representation). Different expressions may be used, for example, to display collected impedance data in various ways (e.g., in various data plots, such as a complex impedance plot and a complex modulus plot) on a graphical user interface (e.g., GUI 14).

Figure 16:
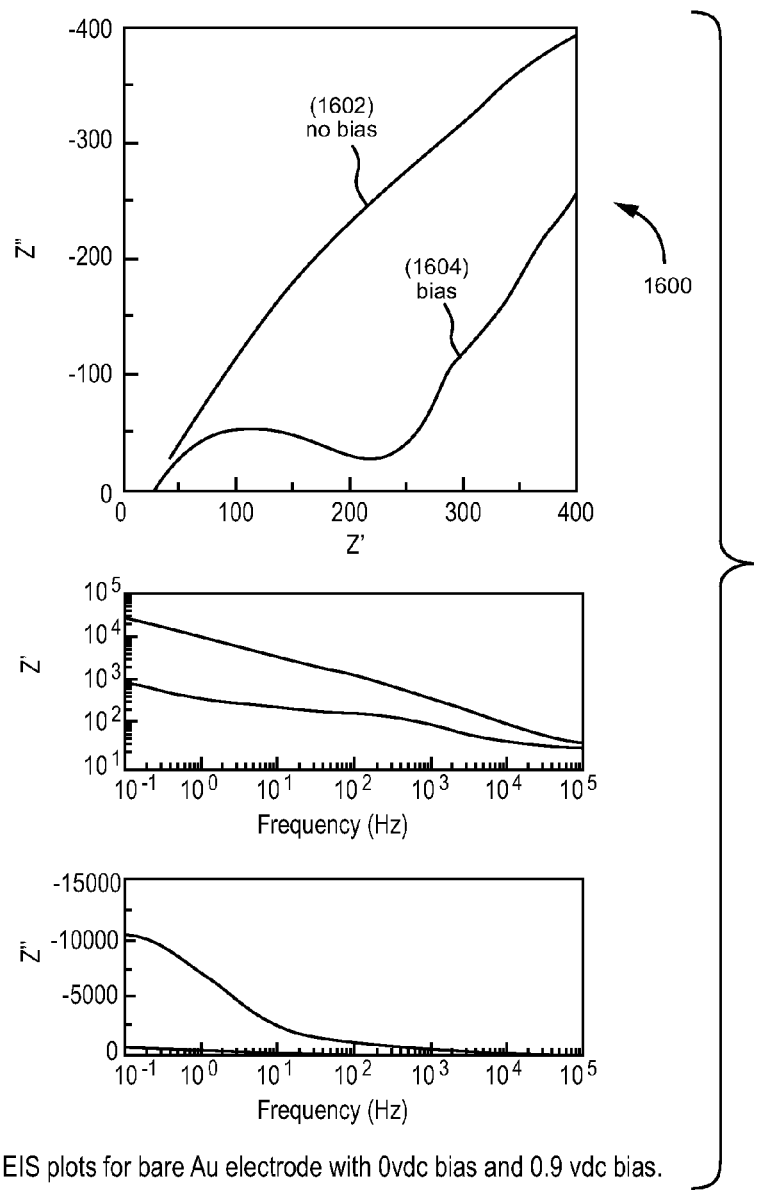
FIG. 16 shows EIS plots for bare Au electrode with 0 vdc bias and 0.9 vdc bias.

FIG. 16 provides the resistance ($R_s$) plotted against the reactance ($1/(\omega C_s)$) (e.g., a plot of complex impedance), which provides an indication of the resistivity of the sample at a given frequency. As a result, the impedance spectra can be used to identify the presence and/or concentration of a target biomolecule (antibody/antigen conjugate) in a sample. FIG. 16 illustrates experimental data showing the effects of DC voltage bias on impedance reading data. In the Z" vs Z' plot 1600, an upper trace 1602 is a trace of sensor readings over a frequency sweep with a 0 vdc bias, and a lower curved trace 1604 illustrates comparable readings with a 0.9 vdc bias. Low frequency data are on the right side of the plot and higher frequencies are on the left. This is true for EIS data when impedance falls as frequency rises. On the Nyquist plot, the impedance can be represented as a vector of length |Z| and f is the angle between this vector and the x-axis. The Nyquist plot for a Randles cell is a semicircle. The resistance can be found by reading the real axis value at the high frequency M' intercept. This is the intercept close to the origin of the plot. The real axis value at the other (low frequency) intercept equals the sum of the polarization resistance and the solution resistance. The diameter of the semicircle is therefore equal to the polarization resistance.

Figure 9A:
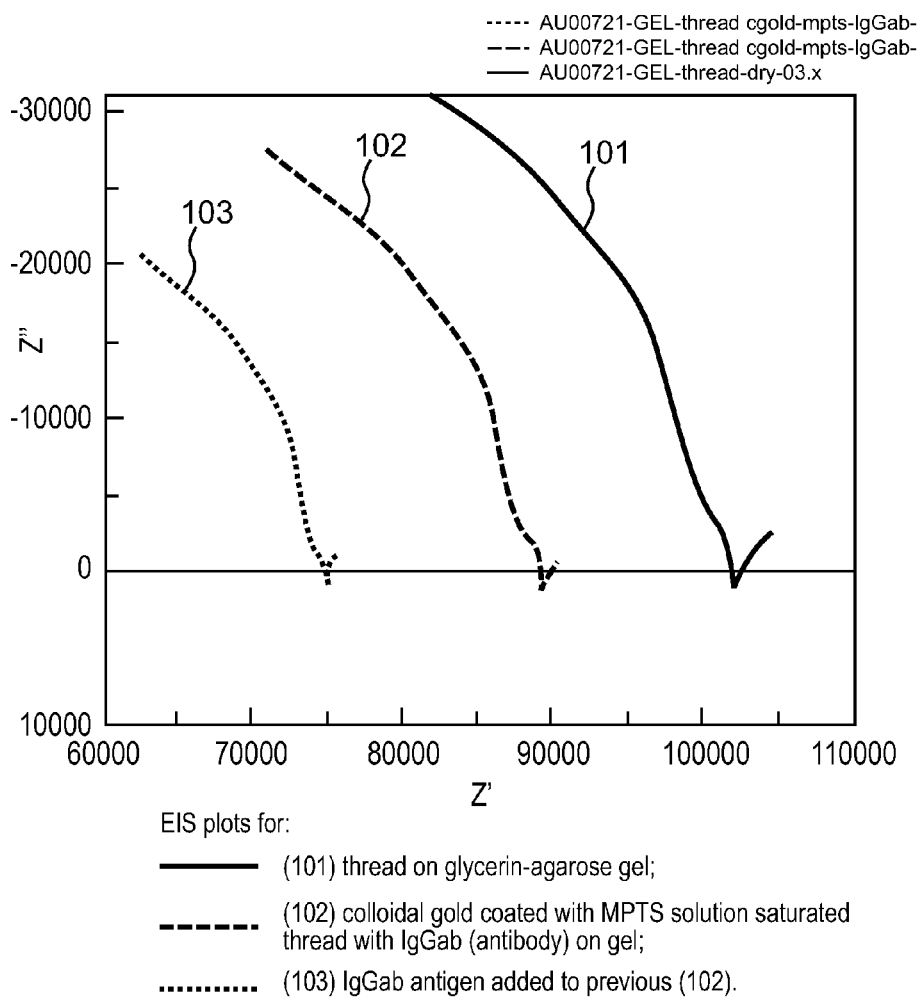
FIG. 9A shows electrical impedance spectroscopy (EIS) Bode plots for linear serial configuration: thread only (101) on glycerin-agarose gel; same thread saturated with colloidal gold coated with MPTS having IgGab (antibodies) attached (102); thread (102) after exposure to IgG antigen (103).
Figure 9B:
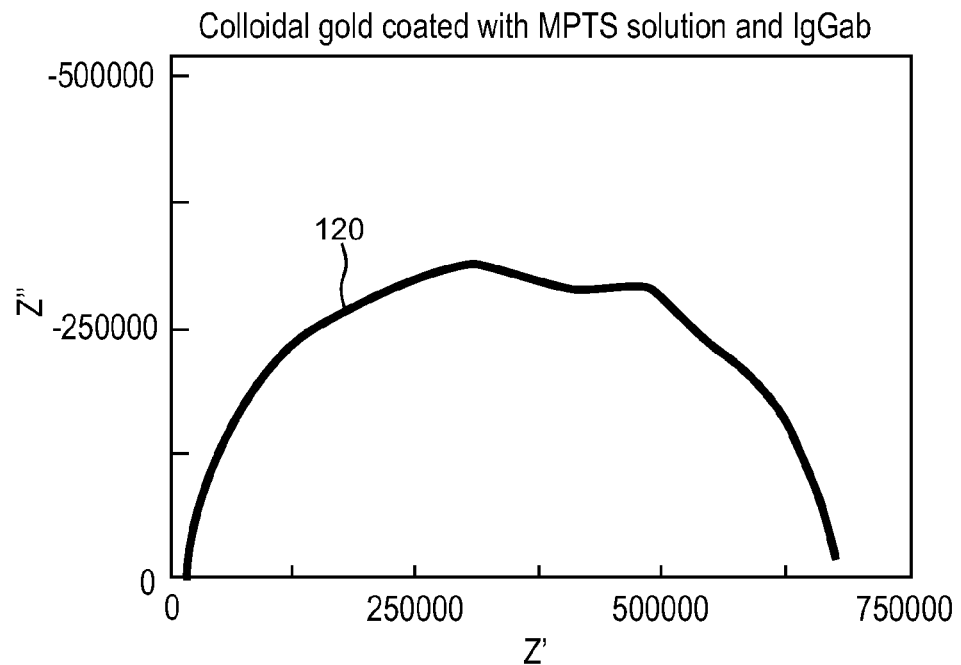
FIG. 9B shows an impedance plot of colloidal gold coated with MPTS solution and IgGAb.
Figure 9C:
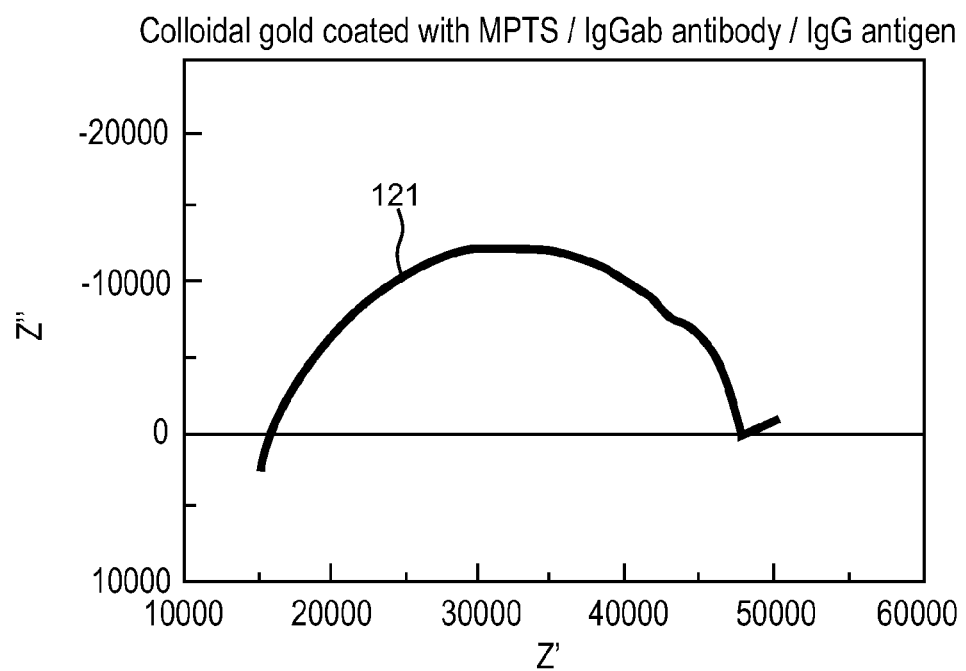
FIG. 9C shows an impedance plot of colloidal gold coated with MPTS/IgGab antibody/IgG antigen.

FIG. 9A shows electrical impedance spectroscopy (EIS) Bode plots of resistance versus reactance for a linear serial configuration according to an exemplary embodiment. The data shown in FIG. 9A may represent measurements by a sensing component over a range of frequencies. Data plot 101 corresponds to a thread only on glycerin-agarose gel. Data plot 102 corresponds to the same thread saturated with colloidal gold coated with MPTS having IgGab (antibodies) attached, and data plot 103 corresponds to the same thread measured in data plot 102, but after exposure to IgG antigen. Comparison of data plots 102 and 103 clearly illustrates that the measured complex impedance for the thread is substantially different before the antigen is added (shown in data plot 102) than after the antigen is added (shown in data plot 103). FIGS. 9B and 9C illustrate expanded data plots 120 and 121 of measured data for a thread before and after the introduction of an antigen, respectively, according to exemplary embodiments, and FIGS. 9B and 9C further illustrate the effect the addition of an antigen has on the measured impedance of the thread.

Figure 10:
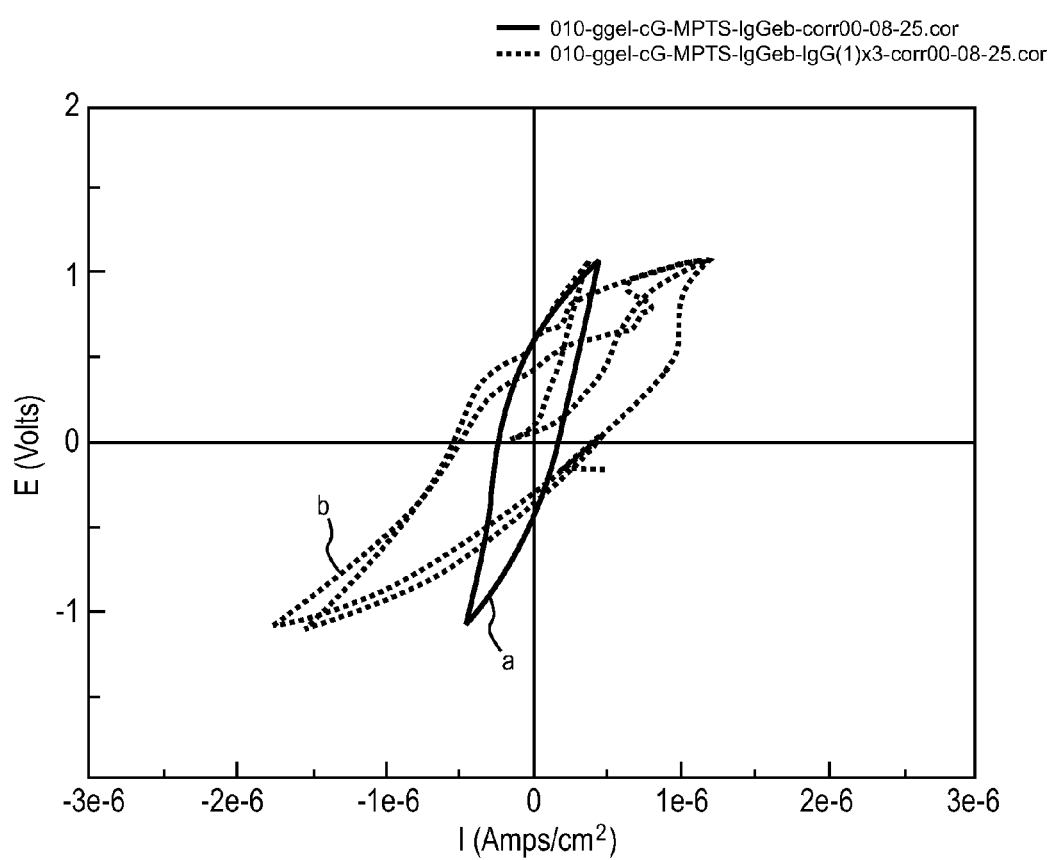
FIG. 10 shows cyclic voltammetry measurements for (a) colloidal gold coated with MPTS with attached IgGab antibodies; (b) after exposure to IgG antigen.

FIG. 10 shows cyclic voltammetry measurements for (a) colloidal gold coated with MPTS with attached IgGab antibodies, and (b) after exposure to IgG antigen according to exemplary embodiments. To generate a cyclic voltammetry plot, the potential or voltage of a working electrode may be ramped linearly over time. Once a predetermined potential is reached, the potential ramp may be inverted. This process may be repeated several times. Again, FIG. 10 illustrates that there are detectable differences in data obtained before an antigen is introduced (plot a) and after an antigen is introduced (plot b).

Figure 11:
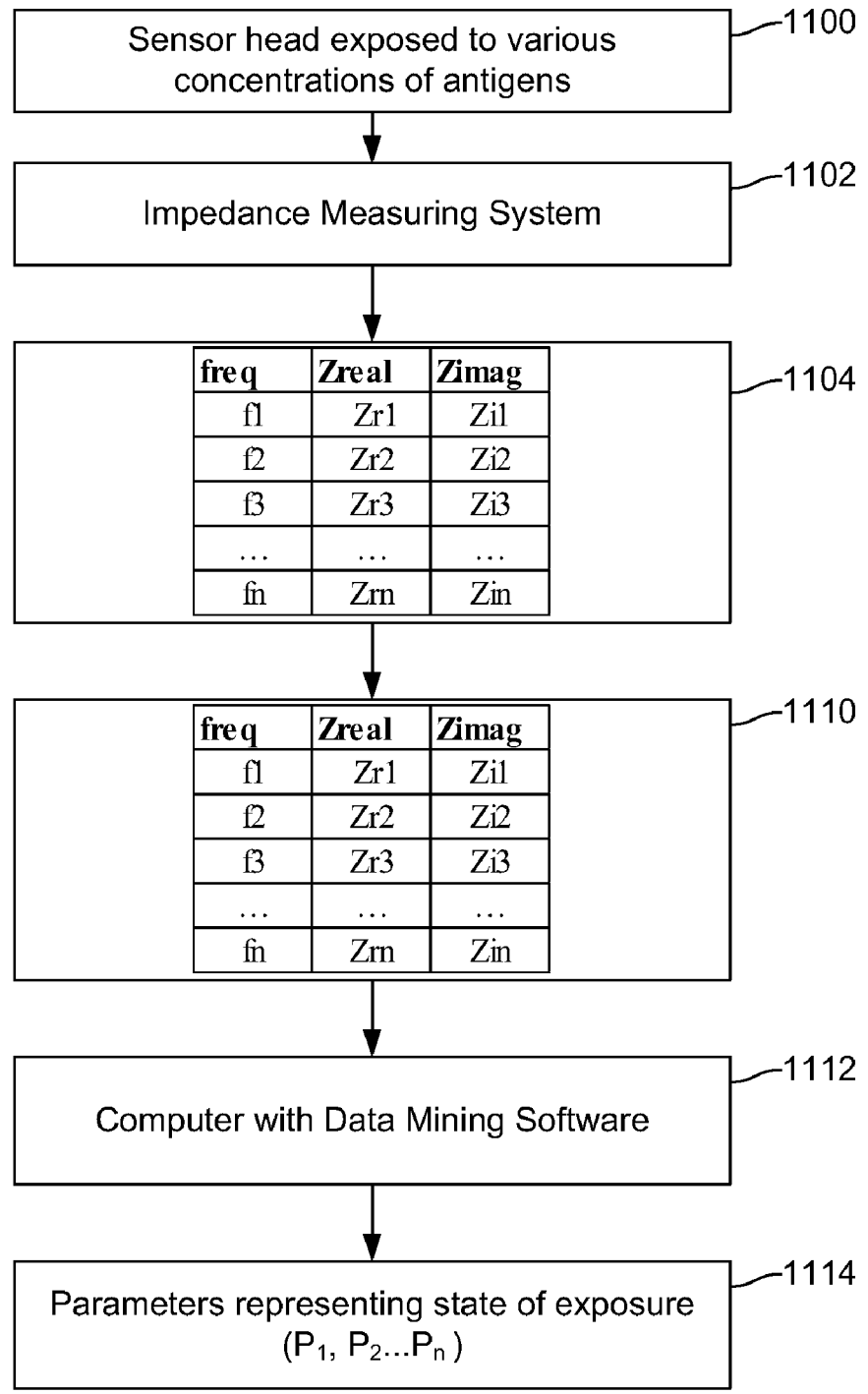
FIG. 11 shows a flow diagram of the sequence of events to analyze a sample, from generating measurement parameters to detection to user display output.
Figure 11:
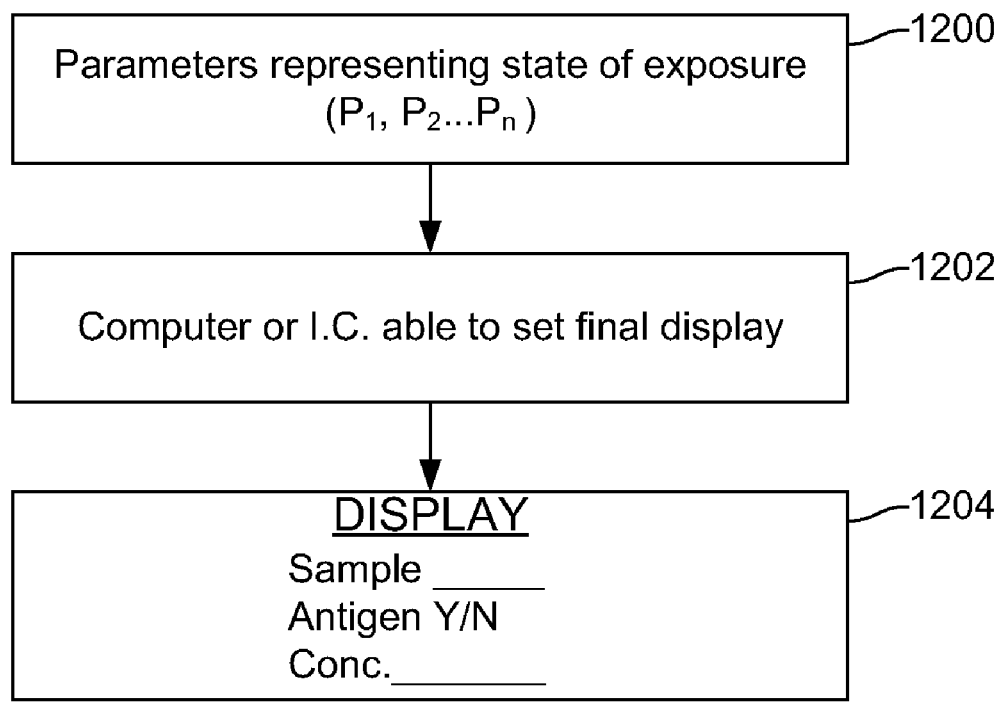

Referring now to FIG. 11, a graphical flow diagram illustrating a sequence of events for analyzing a sample is shown, according to an exemplary embodiment. At step (1100), a sensor is exposed to one or more samples that are to be analyzed. At step (1102), the sensor is configured to measure impedance data relating to the samples over a range of frequencies (e.g., $f_1, f_2, f_3, \ldots f_n$) and to store the data in a memory (at step 1104). In some embodiments, the data may be stored in a complex impedance format and/or by complex impedance components (e.g., a real component and an imaginary component). In other embodiments, the data may be converted to and/or stored in a complex modulus format.

At step (1110), the impedance measurement data which was collected at steps (1102) and (1104) may be mined using a computing device at step (1112). The mining computing device may be the same computing device on which the data is collected (at step 1102) and/or may be transmitted to or loaded onto a separate computing device for data mining. The data mining process at step (1112) involves selecting certain data points to be reference data from among the impedance measurement data collected at step (1102) for use in a detecting device (such as a handheld device). The reference data may be compiled (e.g., provided by a third party, previously created, etc.) by taking measurements relating to exposure to one or more known antigens over a range of frequencies. In some embodiments, all data points collected by the sensor at step (1102) are stored as the reference data for use in later comparison. In other embodiments, only certain selected points (e.g., parameters) may be stored as reference data for use in later comparison. As a result, parameters P1, P2, . . . Pn are generated and stored in a memory at step (1114), which can then be loaded onto a handheld device for use in the field.

The parameters Pn may be established by data mining the EIS Nyquist plot data to describe important points of frequencies sufficient to describe the curves of interest relating to the antibody and antibody-antigen conjugates of interest. Typically these would include peaks of the semicircles of Z', and Z' intercepts or other deflection points. These may represent states of antibodies—e.g. bound or unbound. In some embodiments, the Z" zero intercept will be sufficient to identify reactions as it represents the crossover at a unique frequency, example 3 kHz., from the bulk properties to the electrode analyte interface.

At step (1200), the parameters or data points P1, P2, . . . Pn representing one or more states of antigen exposure (e.g., bound or unbound) are stored in a memory in a computing device, such as a handheld computing device, as reference data. At step (1202), the computing device is configured to compare data acquired from a sensor coupled to the computing device when exposed to a sample to the reference data stored in memory. Impedance measurements made by the handheld device at step (1202) may be compared to corresponding reference data points (e.g., data points for the same frequency) in the reference data set. The handheld computing device may provide frequencies for all or only a subset of the frequencies represented by the reference data points. The handheld computing device may further provide one or more bias signals (e.g., a DC bias voltage) as described herein. Once the collected data is compared to the reference data, a determination is made as to whether the antigen is present in the sample. Further, a determination may be made as to the concentration of the antigen in the sample. This information may be displayed to a user (e.g., on a graphical user interface) optionally along with other data (e.g., sample identification, time of day, temperature at time of sampling, etc.). The display may indicate, for example at step (1204), an identifier (e.g., number) associated with the sample, whether or not an antigen was present in the sample, and/or the concentration level of the antigen present in the sample.

Steps (1100)-(1114) may occur in a laboratory or research environment using computing devices having higher processing and/or memory capabilities (e.g., servers, mainframe computers, or even desktop computers). Steps (1100)-(1114) may be used to identify parameters which can then be loaded into firmware or other memory in handheld devices (or in a memory chip accompanying a sensor package) which are custom-designed to detect certain types of antigens. Steps (1200)-(1204) may then be implemented on a much smaller subset of frequencies, to identify the presence or absence of select points on the graphs of impedance measurements shown in the figures herein.

In some embodiments, the number of impedance parameters stored in the memory of the handheld device or other measurement computing device will depend on the particular biological binding pair that is selected. In general, the number of parameters will be sufficient to recognize the specific binding event of target biomolecules to the capture biomolecules and distinguish this from the background impedance changes that occur when non-target biomolecules are present in the gel, in the vicinity of, but not bound to the capture molecules. For example, for one particular binding pair, 10 to 20 parameters (e.g., measurements corresponding to different frequencies) may be measured, stored, and/or compared with the reference data. For another binding pair, 80 to 100 parameters may be measured, stored, and/or compared with the reference data (e.g., if it is determined that more parameters are needed to adequately detect the presence of the antigen in the second binding pair). In some embodiments, the number of impedance parameters stored in the memory may be between about 10 to about 20, or may be less than 10, less than 50, less than 200, etc. In some embodiments, the range of values of the impedance parameters stored in the memory may be between about 1,000 ohms to 40,000 ohms with ranges of from 200 ohms to 100,000 ohms.

In some embodiments, a biosensor may be tested in a laboratory environment in the presence of an antigen. The biosensor may be operated over a range of frequencies to generate an impedance plot such as that shown in FIG. 9. One or more points on the plot may be selected as parameters. The parameters may comprises parameter data including frequencies and corresponding impedances, for example real and imaginary. The parameters may then be stored in a memory card and loaded into a handheld unit. The handheld unit may be configured to receive a biosensor configured in the same manner as the biosensor used in the laboratory environment. The handheld unit, presumably having less processing power or to be used in a scenario requiring a shorter operation time than in the laboratory, may be configured to transmit to the sensor discrete frequencies based on the preselected or predetermined parameters through the sensing component. The handheld unit may read and store impedances at the selected frequencies and compare the read impedances to the pre-stored impedances. A comparison circuit within the handheld unit is configured to determine whether the read impedances are sufficiently close to the pre-stored impedances (for example, within a predetermined tolerance) so as to make a determination that the antigen is present. If so, an alert or notification message is sent to the GUI. The sensing component may need to be replaced in the handheld unit for future readings.

Figure 5:
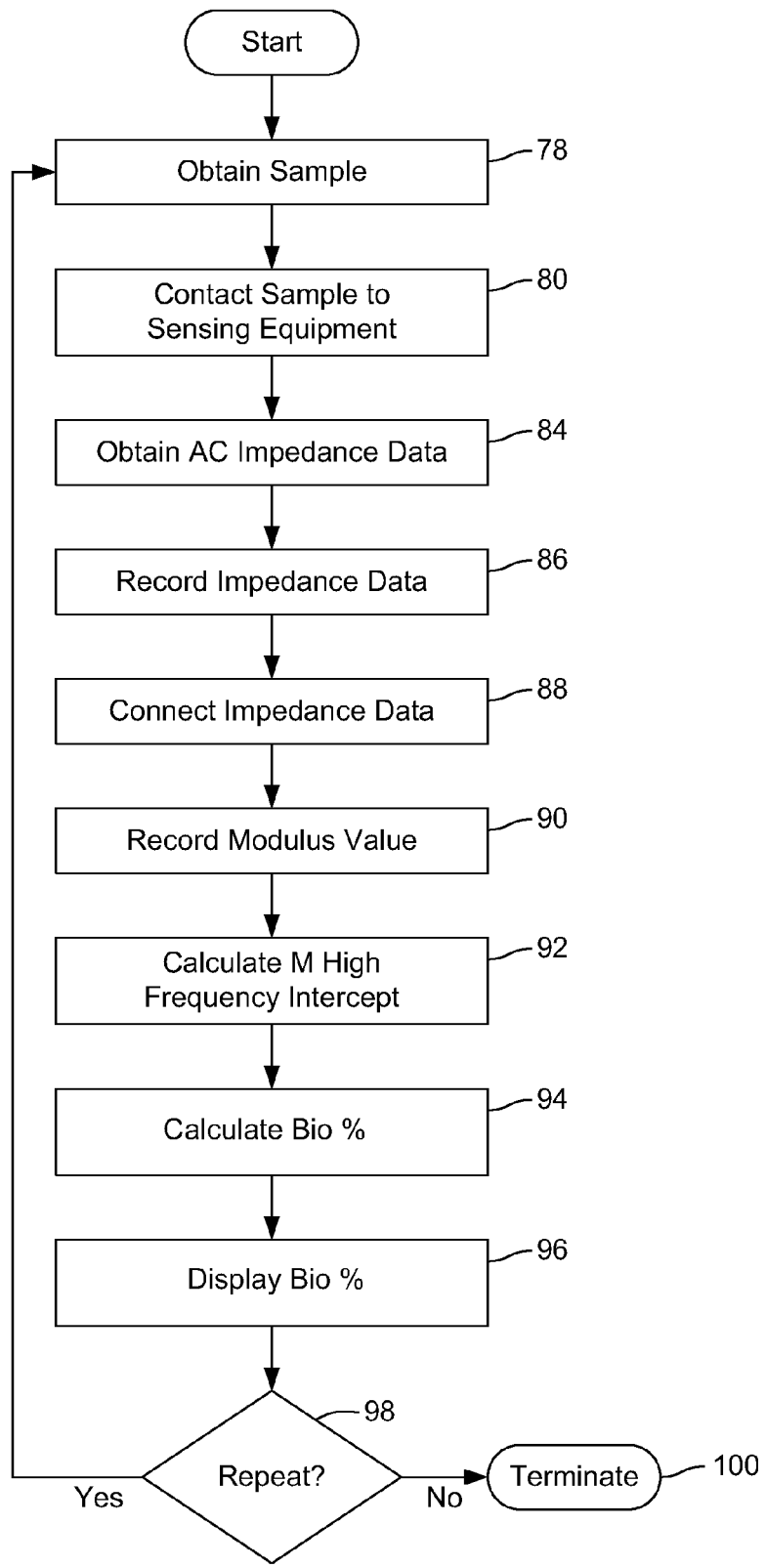
FIG. 5 is a flow chart representing a method for analyzing a biological sample in accordance with an embodiment of the disclosed methods and apparatuses.
Figure 22:
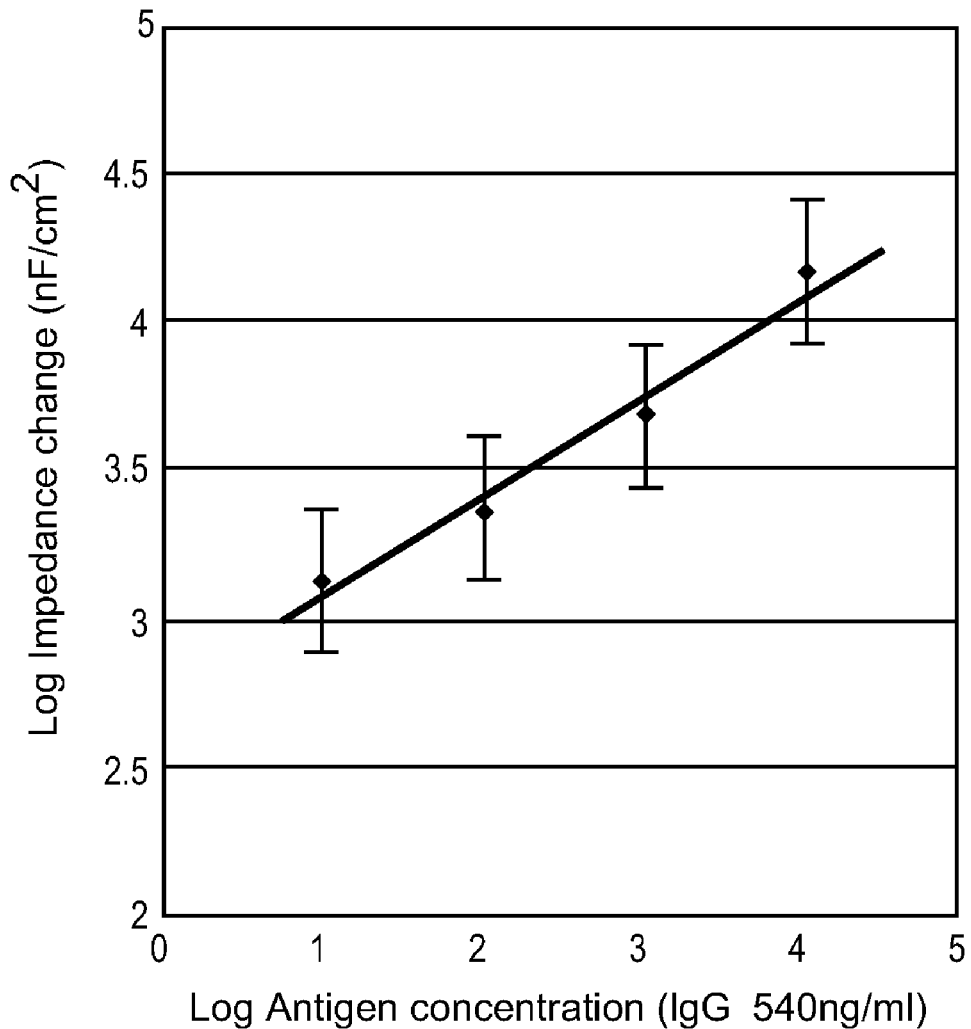
FIG. 22 shows a log plot of IgG concentration vs. og change in impedance, according to an exemplary embodiment.

The biosensors disclosed herein may provide a simple, rapid, specific and direct detection tool for airborne biomolecules. One exemplary embodiment of a method of using the biosensor disclosed herein is provided in the schematic in FIG. 5. As shown in FIG. 5, a sample is obtained (78) and contacted with the sensing component (80). AC impedance characteristics of the sample are obtained (84). The frequency range may extend from about 10 milliHertz to about 100 MegaHertz, or alternatively appropriate frequencies or frequency ranges. The impedance data is recorded (86). The data can be saved in a memory device integral to the device and/or in an external memory device. At step (88) the impedance data is converted to complex modulus values. The complex modulus values are recorded at step (90). The M1 high frequency intercept values are determined at step (92) from the complex modulus values, and the presence/absence and or amount of the biomolecule of interest of the target biomolecule is calculated at step (94). M1 is the high frequency modulus zero intercept of the Nyquist EIS plot. The target biomolecule concentration value is represented on a user interface at step (96). The target molecule concentration value is determined by the linear regression equation from the concentration calibration data (FIG. 22). If the process continues, steps 78 through 98 are repeated, otherwise the sequence is terminated at step 100.

The speed and simplicity with which results are achieved, as compared to standard laboratory assays and tests, make these biosensors an useful tool for a wide range of applications. For example, the biosensor disclosed herein can be used in the interest of national security and community safety and can be employed to detect airborne pathogens such as bacteria such as *Bacillus anthracis*, *Mycobacterium tuberculosis*, *Yersinia pestis* (plague), *Burkholderia mallei* (glanders), *Burkholderia pseudomallei* (melioidosis), *Francisella tularensis* (tularemia), toxic or harmful molds such as, without limitation *Chaetomium Atrobrunneum*, *Fusarium*, *Aspergillus Versicolor* and *Aspergillus Fumigatus*, *Penicillium*, and *Stachybotrys*, waterborne pathogens, such as *Cryptosporidiidae cryptosporidium* and *Vibrio cholerae*, and viruses, such as Smallpox, Ebola, and Marburg (hemorrhagic fever). See also Linda J. Utrup and Allan H. Frey, "Fate of Bioterrorism-Relevant Viruses and Bacteria, Including Spores, Aerosolized into an Indoor Air Environment Experimental Biology and Medicine," 229:345-350 (2004) Randomline, Inc., Potomac, Md. 20854 and GAO Report to Congressional Requestors GAO-03-139 Federal Bioterrorism IT, entitled "Information Technology Strategy Could Strengthen Federal Agencies' Abilities to Respond to Public Health Emergencies." In the Utrup and Frey article, "mock" pathogens were used to determine the nature of the distribution of bacteria and viruses throughout a room with normal ventilation, electrical conduits, etc. The biosensors disclosed herein may have use in monitoring for "sick building" conditions, for example, testing for the types of molds that grow on walls, under carpets, etc., i.e., molds that produce airborne spores which lead to allergic reactions in some people.

According to some exemplary embodiments, the biosensors disclosed herein may include advantages over previous biosensors. For example, in some embodiments, neither the sample nor the detection reaction are liquid-based. Thus, while a liquid sample could be used in the disclosed biosensors, a liquid sample is not necessary. In some embodiments, the disclosed biosensors can detect airborne biomolecules immediately and directly from the environment of interest without the need for sample preparation or reaction preparation. While some pathogens are waterborne, parasitic, survive mainly in vivo or are transferred only by bodily fluids (e.g., are not airborne), biomolecules produced or derived from such pathogens may be present in air samples adjacent to or in proximity to the infected subject (e.g., the exhaled air of an infected patient, or the air in a hospital unit housing infected patients) or a potentially contaminated substance (e.g., air immediately above a water supply, food source, etc.). Thus, in some embodiments, the air environment surrounding substances such as water and food products (e.g., meat, vegetables, grains, dairy products, etc.) is tested using the biosensors disclosed herein for the presence of pathogens or other contaminating agents known to affect such food products.

By way of example, but not by way of limitation, biosensors are configured to detect biomolecules specific to *Escherichia coli* O157:H7, for example by providing an antibody specific to this *E. coli* strain on the sensing component. Such antibodies are known in the art and are commercially available. One or more air samples are collect, for example, from above a meat processing counter, above or near a piece of meat, in a storage facility, a transport container, or within a cavity of the animal(s) being processed. The air sample contacts the sensing component, and if the biomolecules (e.g., antigens that bind specifically with *E. coli* O157:H7 antibodies) are present, a change in impedance, which is characteristic of the biomolecules biding the antibodies, is detected and provided to the user, for example on a display screen as a readout.

In another non-limiting example, biosensors are configured to detect biomolecules specific to *Salmonella* sp. bacterium. Air samples in food processing areas, such as meat processing and/or meat packaging venues, fruit and vegetable processing, and/or dairy production and processing are collected into the biosensor and contacted with the sensing component. In this exemplary embodiment, the sensing component includes capture molecules (e.g., antibodies) specific for *Salmonella*. If biomolecules that specifically bind the antibodies are present in the sample, a characteristic change in impedance is detected and the user is alerted.

The biosensors disclosed herein do not require any sample preparation for use, and no detection reactions need be prepared. Thus, the disclosed biosensors may provide for the rapid, on-site detection of biomolecules of interest.

For example, in some embodiments, the biosensors may provide information on the presence and/or amount of the biomolecule of interest (readout) in less than about 1 minute to about 1 minute, from the time a captured sample is contacted with the sensing component. In some embodiments, the elapsed time from sample capture to readout is less than about 2 minutes, less than about 3 minutes, less than about 4 minutes, less than about 5 minutes or less than about 10 minutes. In some embodiments, the elapsed time from sample capture to readout is between less than about 1 minute to about 10 minutes, less than about 1 minute to about 5 minutes, or less than about 1 minute to about 2 minutes. In some embodiments, the elapsed time from sample capture to readout is between about 1-2 minutes, 1-3 minutes, 1-5 minutes 1-10 minutes, or 1-30 minutes.

Sample capture can be done passively (e.g., by letting the biosensor sit in a particular environment for a period of time, or by passing the biosensor through the air, etc.) an/or by using a sample capture device. For example, in some embodiments, the biosensor can be affixed in a building, for example, in an air duct, and the read out can be transferred to a GUI at a separate location, or can be any number of alerts detectable by a user, e.g., a auditory alarm, a flashing light, or a digital display to indicate the presence and/or amount of the biomolecule to be detected, etc.

In some embodiments, a sample capture device is used. In some embodiments, a sample capture device, includes a vacuum or suction mechanism to more rapidly draw an air sample into contact with the sensing component. The sample capture device can be configured to obtain samples from difficult to reach areas or to obtain samples from areas that may be contaminated with a toxic or harmful substance. For example, the sample capture device may be configured as a rigid, semi-rigid or flexible hose to capture samples within a wall space, in duct work, sewers, filtration systems, areas of collapsed buildings, etc.

In some embodiments, air samples are provided directly to the sensing component; additionally or alternatively, in other embodiments, air samples are stored for a time, and then are provided to the sensing component.

In some embodiments, the volume of air, and/or the amount of time necessary to collect the sample will vary, depending on the likely level of contamination, the biomolecule to be detected and whether a sample capture device is employed and how much suction the sample capture device deliver. For example, in some embodiments, with or without a sample capture device, an air sample is collected for about 1-5 seconds, about 1-10 seconds, about 1-20 seconds, about 1-30 seconds or about 1-60 seconds. In other embodiments, an air sample is collected for about 5-10 seconds, about 5-20 seconds about 5-30 seconds about 5-60 seconds. In other embodiments, an air sample is collected for about 1-2 minutes, about 1-3 minutes, about 1-5 minutes or about 1-10 minutes. In still other embodiments, an air sample is collected for up to about 30 minutes, about 45 minutes, about 60 minutes, about 2 hours, about 3 hours, about 5 hours, about 6 hours, about 8 hours, about 12 hours or about 24 hours. In further embodiments, an air sample is collected for a week, two weeks, or for a month or more. Additionally or alternatively, in some embodiments, an air sample is collected until the biomolecule of interest is detected. This may occur very quickly (e.g., in less than a minute), or it may take more time (e.g., a matter several minutes, several hours, several days, weeks or months).

As used herein, the term "antibodies" means antibodies, including monoclonal and polyclonal antibodies, single chain antibodies, Fab fragments, recombinant antibodies, and the like, that specifically bind a particular target biomolecule. Antibody fragments that specifically bind the target biomolecule also can be used. Protocols for producing antibodies, both polyclonal and monoclonal, are well known in the art and are described, for example, in Ausubel, et al. (eds.), Molecular Cloning: A Laboratory Manual, Cold Spring Harbor Laboratory, (Cold Spring Harbor, N.Y.), Chapter 11; METHODS OF HYBRIDOMA FORMATION 257-271, Bartal & Hirshaut (eds.), Humana Press, Clifton, N.J. (1988); Vitetta et al., Immunol. Rev. 62:159-83 (1982); and Raso, Immunol. Rev. 62:93-117 (1982).

Polyclonal antibody production can be performed as described in the following example. A target biomolecule, optionally in conjunction with an adjuvant, is diluted in a physiologically-tolerable diluent such as saline, to form an aqueous composition. An immunostimulatory amount of inoculum, with or without adjuvant, is administered to a mammal and the inoculated mammal is then maintained for a time period sufficient to produce antibodies. Boosting doses of the inoculum composition may further enhance this process. Antibodies can be obtained by bleeding the animals and recovering serum or plasma for further processing. Antibodies can be prepared in a variety of commonly used animals, e.g., goats, primates, donkeys, swine, rabbits, horses, hens, guinea pigs, rats and mice, after appropriate selection, fractionation and purification.

Antibodies can be harvested and isolated to the extent desired by well known techniques, such as by alcohol fractionation and column chromatography, or by immunoaffinity chromatography; that is, by binding antigen to a chromatographic column packing like Sephadex™, passing the antiserum through the column, thereby retaining specific antibodies and separating out other immunoglobulins (IgGs) and contaminants, and then recovering purified antibodies by elution with a chaotropic agent, optionally followed by steps to further purify the antibodies. This procedure may be followed when isolating the desired antibodies from the sera or plasma of the inoculated animal, or from an animal that has developed an antibody titer against the antigen in question, thus assuring the retention of antibodies that are capable of binding to the antigen.

A monoclonal antibody composition contains, within detectable limits, only one species of antibody that specifically binds to the antigen. Suitable monoclonal antibodies can be prepared—using conventional techniques, such as hybridoma technology or phage display technology. For example, to form hybridomas from which a monoclonal antibody composition is produced, a myeloma or other self-perpetuating cell line is fused with lymphocytes obtained from peripheral blood, lymph nodes or the spleen of a mammal hyperimmunized with the antigen. The myeloma cell line often is from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA. Balb/C mouse spleen, human peripheral blood, lymph nodes or splenocytes are typically used in preparing murine or human hybridomas. Suitable exemplary mouse myelomas include the hypoxanthine-aminopterin-thymidine-sensitive (HAT) cell lines. For example, a monoclonal antibody composition useful in accordance with the present compositions and methods can be produced by initiating a monoclonal hybridoma culture comprising a nutrient medium-containing a hybridoma that secretes antibodies. The culture is maintained under conditions and for a time period sufficient for the hybridoma to secrete the antibody molecules into the medium. The antibody-containing medium is then collected, and the antibodies can be isolated further by well known techniques.

Alternatively, the monoclonal can be cloned out from the hybridoma cells, phage display techniques, or other known techniques, and inserted into an appropriate expression cell line that can express and produce high amounts of antibodies. These cell lines can include Chinese Hamster Ovary cell line (CHO), insect cells, or other cell lines.

Other methods of preparing monoclonal antibody compositions are also contemplated, such as interspecies fusions. Those skilled in the art will appreciate that it is primarily the antigen specificity of the antibodies that dictates their suitability for use in the context of the disclosed biosensors.

As noted above, antibodies may include whole antibodies, antibody fragments, and/or antibody subfragments. Antibodies can be whole immunoglobulin of any class, e.g., IgG, IgM, IgA, IgD, IgE, chimeric antibodies or hybrid antibodies with dual or multiple antigen or epitope specificities. Fragments can be $F(ab')_2$, Fab', Fab and the like, including hybrid fragments. Other immunoglobulins or natural, synthetic or genetically engineered proteins that act like an antibody by specifically binding to a target biomolecule also can be used. In particular, Fab molecules can be expressed and assembled in a genetically transformed host like *E. coli*. A lambda vector system is available thus to express a population of Fab's with a potential diversity equal to or exceeding that of subject generating the predecessor antibody. See Huse, W. D. et al., Science 246: 1275-81 (1989).

The reactions of interest may be in the close proximity of the surface of the electrode. The Stern layer dominates the electrical sensitivity and when the ions in solution are forced to flow through the single small surface layer, detection of changes in the capacitance of the layer is possible because the signal is well above the noise level.

Figure 12:
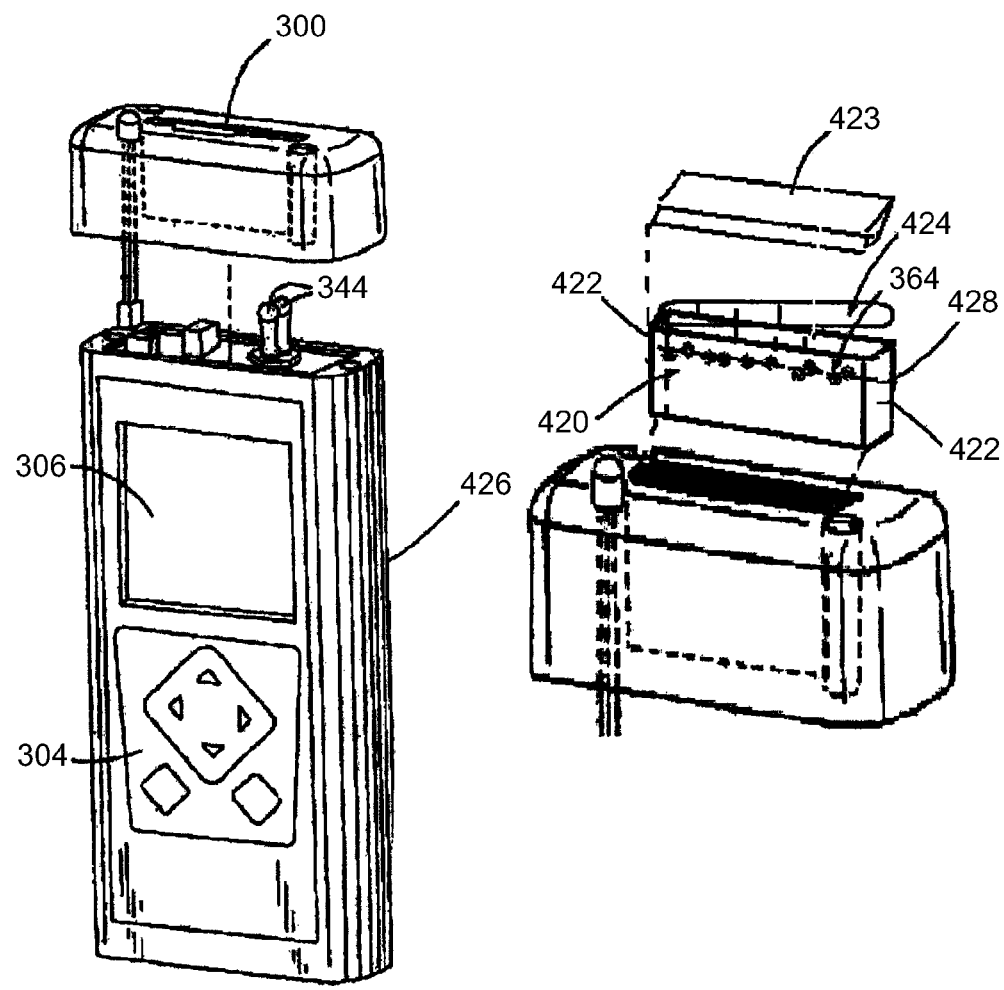
FIG. 12 shows a drawing of a hand-held detection and an exploded view of a detachable/reuseable bioimmunosensor detection module, according to an exemplary embodiment.

A hand-held or portable sensor can be developed by producing a detachable module (300) that can interface to a handheld impedance measurement device (426) as described in U.S. patent application Ser. No. 12/263,064 as in FIG. 12. The hand-held device includes a display (306) and a flat keyboard (304) interfacing at (344). The module can be sealed (424) for biosafety during transit. In addition, the module (300) could be reused by removing the sensor unit (420), disinfecting if necessary, and inserting a new sensor unit. In one embodiment, a seal (424) could be broken to expose the sensor to air and thus activate it. The module can be filled with an electrolytic gel. Metallic electrodes (422) mount inside on the sides of the chamber of the module (420) can be made of, for example, gold or gold coated metal, or stainless steel mesh. A string-like material (428) is attached between to the electrodes and has colloidal gold nano-particles (364) coated with a self-assembled monolayer such as MPTS, and attached on one side to the string-like material (428), and has specific antibodies attached on the other side of the particles, on the ends of the MPTS coating. In another embodiment, an antigen sample could be hermetically sealed in, for example, plastic (423) and then inserted in the sensor module and be released to the sensor unit, without exposure to the user.

Mathematical and statistical techniques, but not limited to, linear regression, neural networks, and "near neighbor" data mining analysis is used to determine detection and eliminate false positives, and algorithms configured to operate such techniques are programmed into a computer-readable memory disposed in the handheld device.

a. An experiment was performed with an antigen in buffer of neutral pH (near 7) below the saturation point (but in the detection range) with positive and negative DC electrical biases (one bias per trial) on the counter electrode. The bias range tested was −2 vdc to +2 vdc in 0.5 vcd intervals. The trials were performed in various orders, to note the effect of the previous bias, e.g. +1, 0, −1; +1, −1, 0; −2, +1, 0, etc.

b. The entire experiment was repeated starting with a higher and lower pHs. The results were plotted. Then, the experiment was repeated starting with the optimal pH, and varying the DC bias during the trial to determine the regenerative properties. FIG. 16 shows the results.

The sensor described shows fine selectivity and sensitivity to nanomole (nM) levels.

Figure 13:
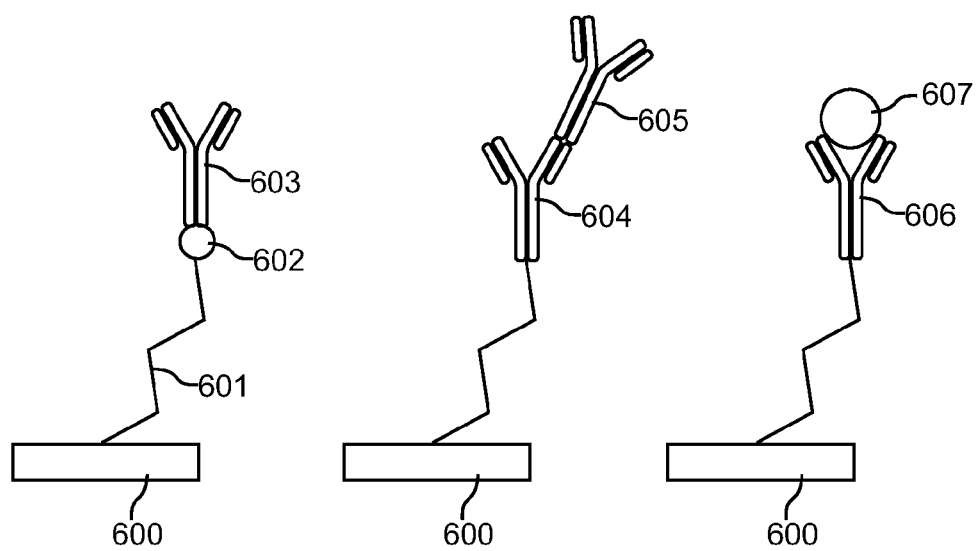
FIG. 13 shows various configurations of antibody attachments.

FIG. 13. In another embodiment, antibodies can be immobilized by using a sol-gel monolayer (601), such as MPTS attached on one end, of each molecule, to a substrate (600), and the other end attached to a colloid bead, such as gold (602). In another embodiment, antibodies (605) can be immobilized by attachment to a different antibody (604) which can attach more securely to the monolayer. In still another embodiment, a specific antigen (607) can be conjugated with the antibody (606) in order to capture other specific antibodies (e.g., instead of an antigen).

Example

Preparation of Capture Molecules

Capture molecules, such as colloidal gold (e.g., 20 nm diameter gold nonaparticles) may be prepared as follows:
1) Mix 200 ml of $H_2O$ and 1.00 ml of 1% $HAuCl_a$
2) Add 1.50 ml of 0.075% $NaBH_4$/1% trisodium citrate and 0.55 ml of 1% trisodium citrate.
3) Stir continuously for 6 hours at room temperature (but store at 4° C. for future use).
4) In a separate container, mix a sol-gel such as MPTS with absolute ethanol and aqueous acid (0.1M HCl) at a molar ratio of 1:4:3.5 and sonicate for 1 hour until it is a homogenous solution.
5) Mix the solution from Step 3 with the solution from Step 4 at room temperature, stirring gently for 10 seconds, then setting in darkness for 12 hours (do not sonicate or disturb). In this step, the self-assembling monolayer will attach to the gold nanoparticles.
6) If a solid, insulating, string-like material is used, submerse it in the solution from Step 5 at room temperature for at least 4 hours undisturbed in darkness. This will covalently attach one side of the SAM coated colloid gold nanoparticles to the polymer string-like material.
7) Add the desired antibody to the results of Step 5 or 6, as applicable, and gently rock for 4 hours.
8) If the string-like material is porous, saturate it with the results of Step 7.
9) In steps 5, 6, & 7, the process can be halted, and then repeated for additional layers, by flushing with a buffer, such as PBS.

Figure 17:
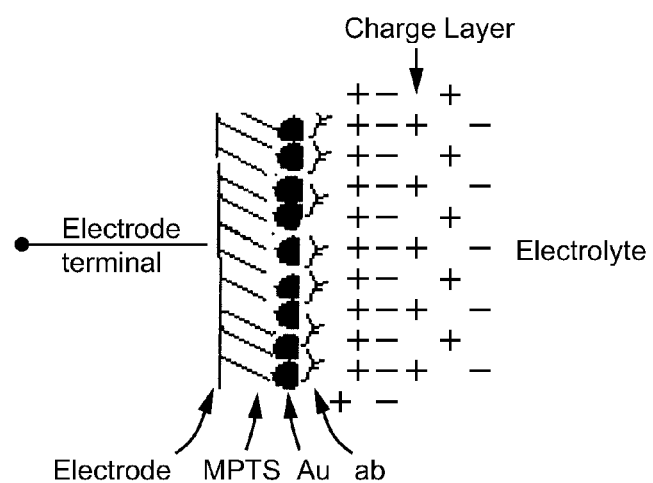
FIG. 17 is a schematic diagram of an electrode-electrolyte interface, according to an exemplary embodiment.

Referring now to FIG. 17, a schematic diagram of an electrode-electrolyte interface is showing, according to an exemplary embodiment. When an electrolyte comes in contact with a metallic electrode, there is an ion-electron exchange. The term "double layer" refers to the displacement of electrical charges associated with the electrode surface exposed to an aqueous solution as in FIG. 17. There is a tendency for ions in the solution to combine with the metallic electrode and also for the metallic ions to enter the solution. The basic type of charge distribution was proposed by Helmholtz (1879) who postulated that there exists a layer of charge of one sign tightly bound to the electrode and a layer of charge of the opposite sign in the electrolyte. This separation is called the electrical double layer and is measured in ionic dimensions. As illustrated in FIG. 17, in the Stern, also called the condensed layer, the ions are aligned against the surface. The Gouy layer is a diffuse atmosphere past the Stern layer. In this layer, the density of ions is given by the Poisson-Boltzmann relationship:

$$C_{St,i}(i) = C_L(i) \cdot \exp\left\{-\frac{z(i) \cdot F}{R \cdot T} \cdot \psi_{St,i}\right\}$$

where
  $c_{St,i}(i)$ Stern layer concentration of species i (mmol/L)
  $c_L(i)$ concentration in the liquid phase of species i (mmol/L)
  $z(i)$ valency number of species i (eq/mol)
  F Faraday constant (C/mol)
  R Boltzmann constant (1.38×10−23 J/K mol)
  T temperature (K)
  $\psi_{St,i}$ electric potential of i th Stern layer (V)
and the Debye length equation:

$$\lambda_D = \sqrt{\frac{\varepsilon RT}{F^2 \frac{1}{2}\sum_i c_i z_i^2}}$$

where
  F electron charge (1.6×10$^{-19}$ C)
  $\in$ relative dielectric constant for water at 25 C times the permittivity in vacuum (8.854×10$^{-12}$ C/V-m)
  $n_i$ ion concentration (ions/m$^3$)

The double layer effect extends about 10 nm from electrodes, where beyond there is usually an equal density of positive and negative ions.

Figure 18:
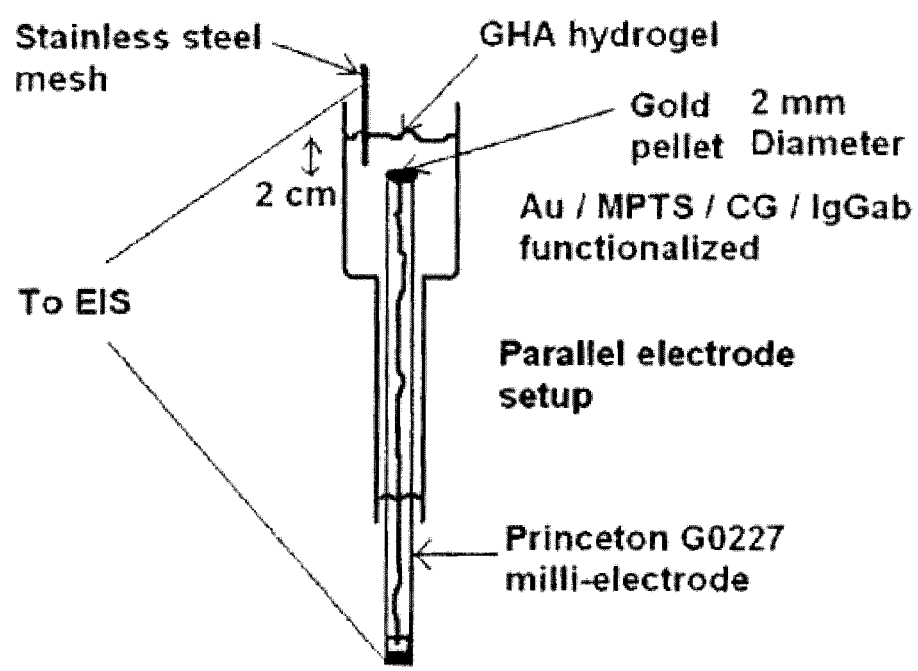
FIG. 18 is a schematic diagram of an experimental setup for testing a parallel mode electrode.

Referring now to FIG. 18, a schematic diagram of an experimental setup for testing a parallel mode electrode is shown. A plastic eyedropper was cut off at the top and bottom as a container for the gel based sensor. An electrode made of stainless steel mesh was placed on the top surface of the previously described hydrogel mixture. This was a mesoporous/macroporous hydrogel. In this instance, agarose 2% mixed with glycerin (the mixture referred to as GHA) was used.

An MPTS/IgGab coated, EG&G Princeton M0227 milliprobe with a 2 mm in diameter gold pellet on the end, was positioned 2 cm below the top electrode under a layer of gel (see FIG. 18). The specific antigen was introduced on the top, near the stainless steel mesh electrode. EIS measurements were made between the electrodes for 30 minutes as the antigen diffused through the hydrogel toward the bottom gold electrode and became positively detectable.

Figure 19:
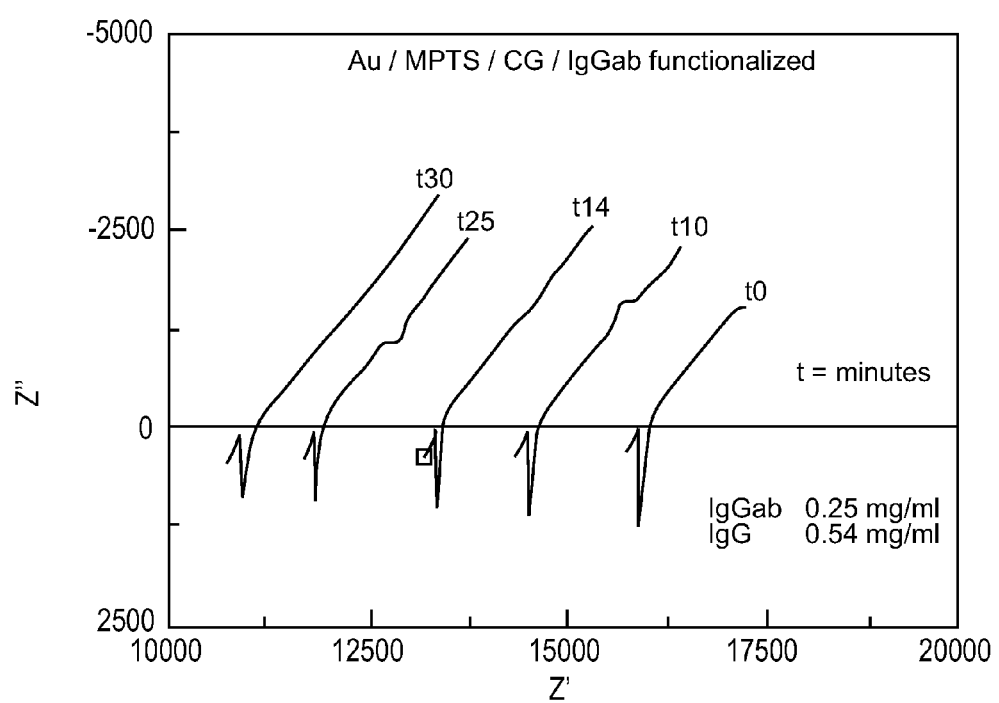
FIG. 19 shows EIS plots for a parallel electrode, according to an exemplary embodiment.
Figure 20:
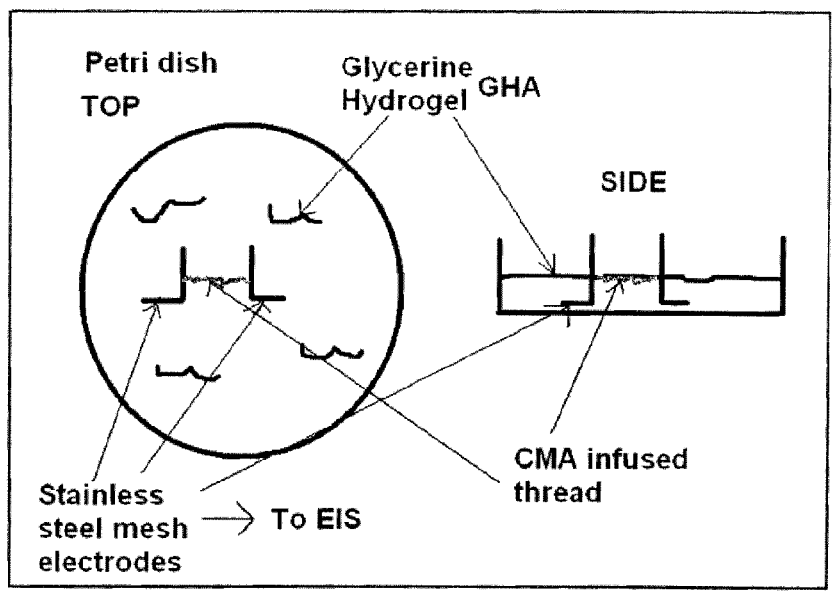
FIG. 20 is a schematic diagram illustrating a linear/serial experiment setup with colloidal gold/MPTS/antibody electrode, according to an exemplary embodiment.

Referring now to FIG. 19, EIS plots for a parallel electrode are shown according to an exemplary embodiment. GHA gel was used to isolate the MPTS/antibody solution from air, and still allow antigens to pass through by diffusion. A forced air delivery system could have been employed, but was not in this experiment; gravity and an eyedropper were utilized. In this experiment, the output was a binary yes/no result. The decrease in Z' over time showed that antibody/antigen conjugation was being detected as in FIG. 19. The representative shape and differential magnitude of the EIS plots eliminate false positives. Our GHA hydrogel is a viable medium for the basis of an immunosensor which can be exposed to air in any orientation and capture antigens which can be detected with a specific antibody functionalized electrode Referring now to FIG. 20, a schematic diagram illustrating a linear/serial experiment setup with colloidal gold/MPTS/antibody electrode in a confining mode is shown, according to an exemplary embodiment. Electric current, through ions, needs to be directed along a path of coated gold nanoparticles of the FDC to be effective and obtain useable detection measurements. Therefore, in order to keep the nanoparticles in line, a confining entity was used. In the parallel embodiment, the gold electrode is the base. In this linear/serial embodiment, to effect the serial arrangement, a thin thread or string-like material was utilized by soaking it with the MPTS coated colloidal gold solution (suspension.) The conductivity and impedance characteristics were then measured over applicable voltage and frequency ranges to provide a baseline for comparison to the electrical characteristics, after exposure to non-specific and/or specific conjugating antigens. Thereafter, the delta measurements were evaluated to determine if specific or non-specific antigens were present.

Figure 21:
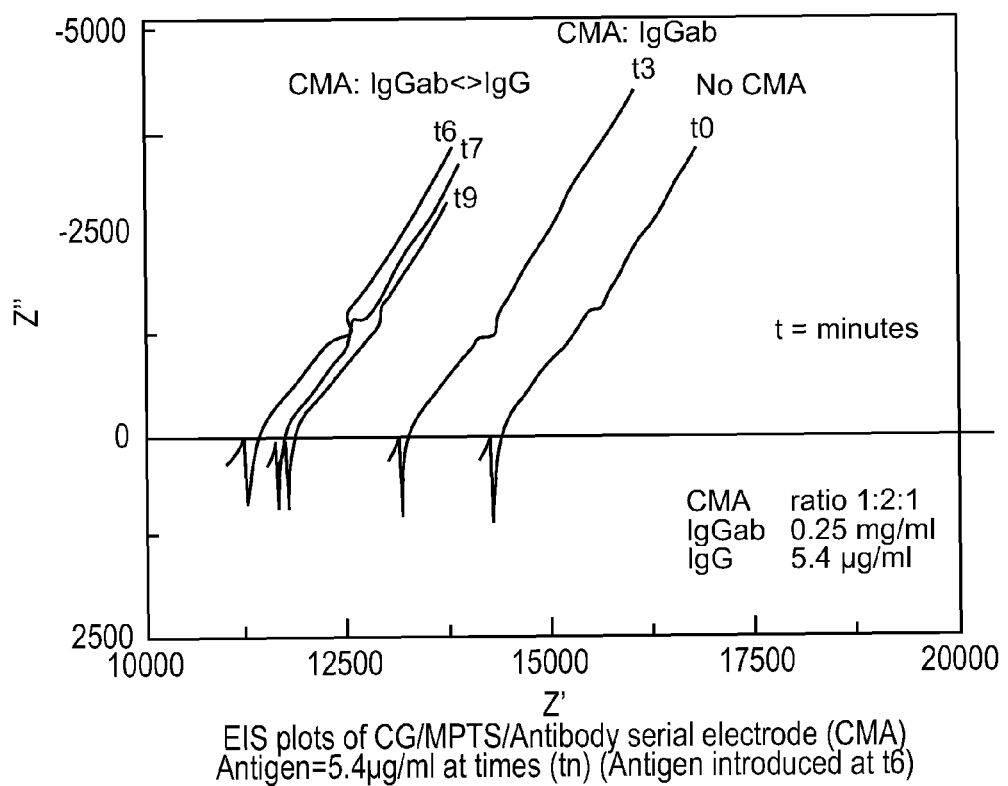
FIG. 21 shows EIS plots of data from the experiment shown in FIG. 20, according to an exemplary embodiment.

The EIS plots of CG/MPTS/Antibody serial electrode (CMA) are shown in FIG. 21. At t0, there is only the confining entity for the electrode. At t3, the CG/MPTS/IgGab is introduced as the electrode. At t6, the antigen IgG was introduced. Times t6 and t7 showed a small diffusion toward equilibrium.

FIG. 22 shows a log plot of IgG concentration vs. log change in impedance, according to an exemplary embodiment.

The Standard Error is calculated as follows:

$$S.E. = \sqrt{\frac{\sum_{s=1}^{m}\sum_{i=1}^{n} y_{is}^2}{(n_y - 1)(n_y)}}$$

where
  s=series number
  i=point number in series s
  m=number of series for point y
  n=number of points in each series
  $y_{is}$=data value of series s and the ith point
  $n_y$=total number of data values in all series The sensitivity of the linear/serial sensor arrangement was determined by subjecting the sensor with CMA to varying concentrations of specific antigens. Between the lower limits of detection and the saturation point, there exists a pseudo-linear region that can be used for calibration of the bioimmunosensor. The CMA with IgGab was measured with EIS in the range of frequencies from 100 kHz to 100 Hz. Multiple readings were taken at active points in the experiment. The initial reading was without CMA, just the confining entity, in this case, polyester thread. The thread was tightly wrapped around and between two stainless steel mesh electrodes approximately 1.5 cm apart. As demonstrated in a previous experiment, the distance, within one standard deviation, does not significantly affect the EIS readings with a given volume of CMA. The CMA was prepared as described above, with a 1:2:1 ratio of 20 nm colloidal gold to MPTS to 0.25 mg/ml IgGab. Each concentration test was performed with 20 µl of CMA and included an EIS reading immediately after introduction to the polyester thread. After the initial drop in real impedance, multiple EIS readings were taken over the next few minutes as the FDU reached equilibrium at a slightly higher real impedance value. This was caused by repulsion of the negative charges of the CMA nanoparticles and diffusion into the GHA hydrogel. A known concentration of antigen (10 µl of IgG) was then introduced onto the FDU and multiple readings of EIS were taken over several minutes as the real impedance value moved upward toward equilibrium. Given the predominantly cationic or positive surface charge of the IgGab, the anionic or negatively charged antigen IgG conjoined with the antibodies, reduced the distance between molecules, and increased the capacitance of each nanoparticle.

Figure 23:
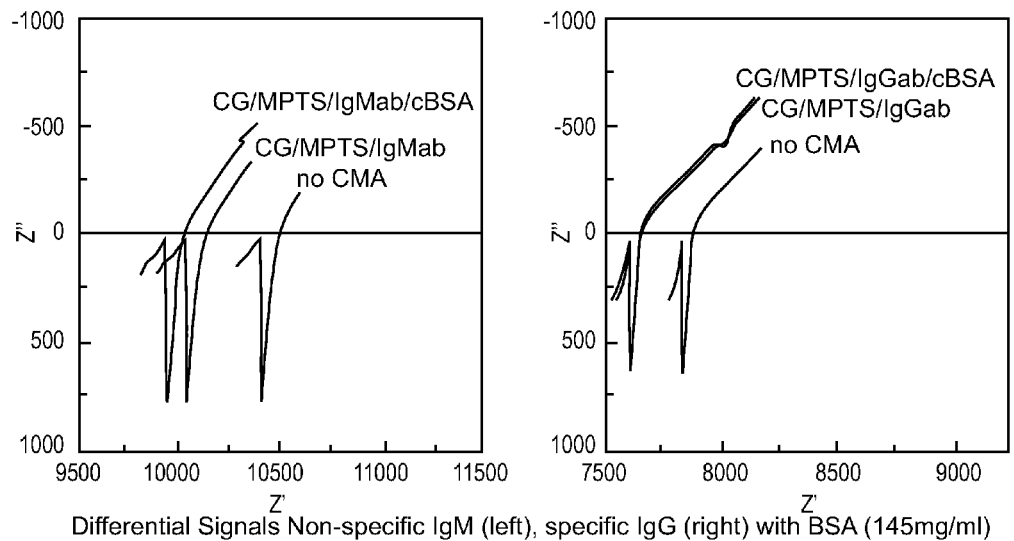
FIG. 23 shows plots of differential signals for non-specific IgM and specific IcG with BSA, according to an exemplary embodiment.
Figure 24:
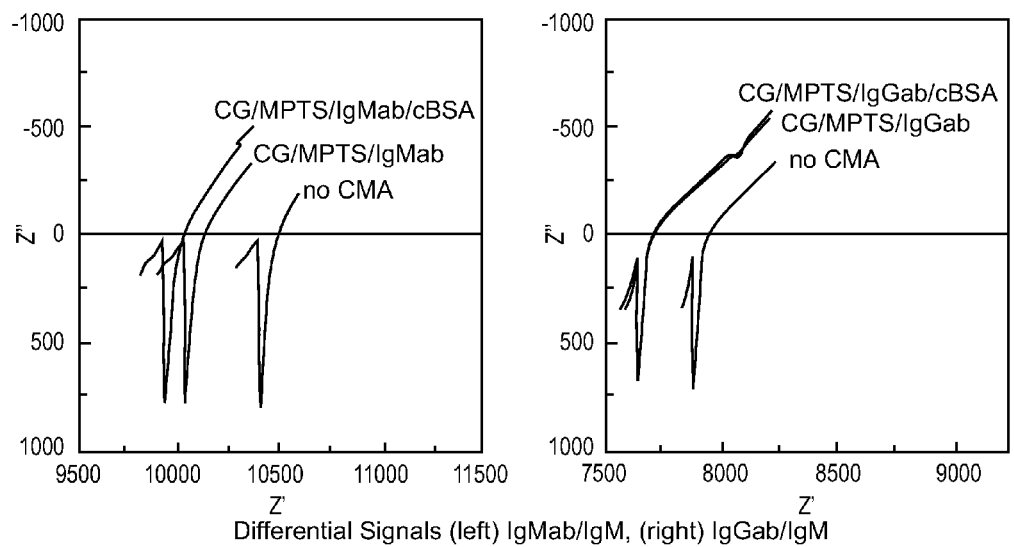
FIG. 24 shows plots of differential signals for IgMab/IgM and IgGab/IgM, according to an exemplary embodiment.
Figure 25:
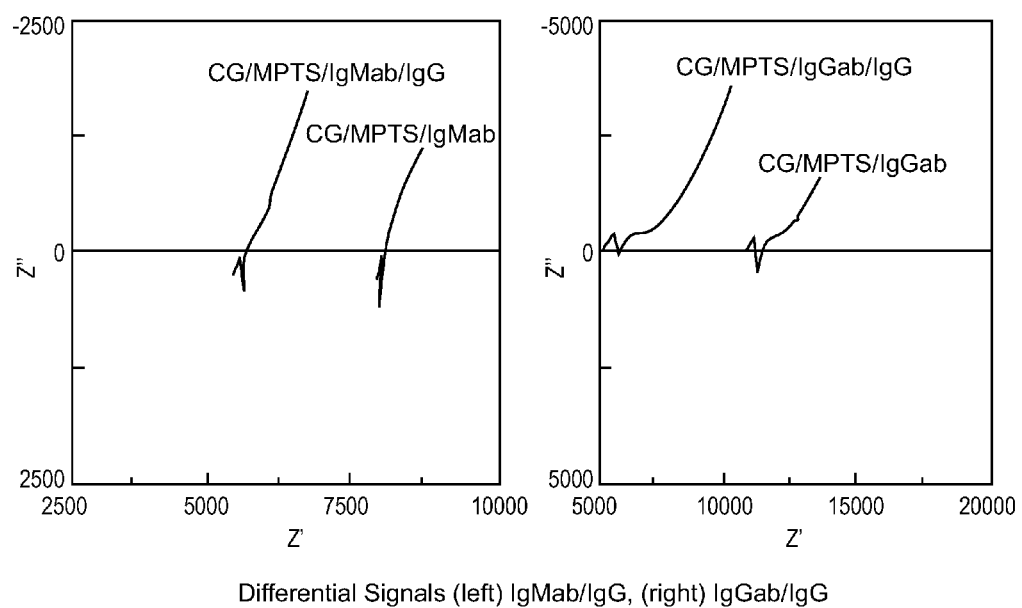
FIG. 25 shows plot of differential signals for IgMab/IgG and IgGab/IgG, according to an exemplary embodiment.

FIG. 23 shows plots of differential signals for non-specific IgM and specific IcG with BSA, according to an exemplary embodiment. FIG. 24 shows plots of differential signals for IgMab/IgM and IgGab/IgM, according to an exemplary embodiment. FIG. 25 shows plot of differential signals for IgMab/IgG and IgGab/IgG, according to an exemplary embodiment. When an antigen was introduced to the immunosensor, if the change in Z of the non-specific antibody FDU was greater or about equal to the change in Z of the specific antibody FDU, that was an indication that the specific antigen was not present as in FIG. 23. If, on the other hand, the change in Z of the specific antibody FDU was much greater than the change in Z of the non-specific antibody FDU, then the specific antigen was present as in FIGS. 24 and 25. Therefore, the comparison of the magnitudes of the measurements reliably indicated if the specific antigen was present or not, and eliminated many false positives.

The processing circuitry described herein may comprise one or more modules, circuits, or other functional units configured to or programmed to perform the functions described herein, including without limitation the algorithms, measurements, and data plotting functions. The processing circuitry in the handheld unit and/or desktop or mainframe environment may comprise one or more analog and/or digital circuit components, such as a microprocessor, microcontroller, application-specific integrated circuit, amplifiers, buffers, A/D or D/A converters, communications circuits, hardware and/or electrical interfaces, connectors, cabling, printed circuit boards or other circuit components arranged to perform the functions described herein, along with suitable memory for storing data as would be needed. The algorithms or functions described herein may be embodied on a non-transitory computer readable medium comprising computer-readable instructions which, when executed, perform the algorithms or functions.

What is claimed is:

1. A biosensor for detecting the presence and/or amount of a biomolecule in a sample, comprising:
   a) a housing;
   b) a sensing component, the sensing component comprising:
      (i) a string-like material contacting an electrolytic gel;
      (ii) colloidal gold nanoparticles linked to the string-like material, wherein the nanoparticles are each coated with a self-assembling monolayer ("SAM"), and wherein a portion of the SAM on the nanoparticles links the nanoparticles to the string-like material and another portion of the SAM on the nanoparticles links the nanoparticles to a capture molecule;
      (iii) at least two electrodes in contact with the electrolytic gel and configured for impedance detection across the electrolytic gel;
   c) an impedance measurement circuit coupled to the electrodes of the sensing component;
   wherein the biosensor is configured to detect the presence and/or amount of the biomolecule in a dry sample in a non-liquid detection reaction.

2. The biosensor of claim 1, wherein the sensing component is configured to sense an air sample.

3. The biosensor of claim 1, wherein the capture molecule comprises an antibody.

4. The biosensor of claim 1, wherein the capture molecule comprises an antibody that specifically binds to a mold antigen.

5. The biosensor of claim 1, wherein the capture molecule comprises an antibody that specifically binds to an antigen which has been bound to another antibody.

6. The biosensor of claim 1, wherein the capture molecule comprises a monoclonal antibody that specifically binds to a mold antigen, wherein the mold is selected from the group consisting of the genus *Chaetomium*, *Aspergillus*, *Penicillium*, and *Stachybotrys*.

7. The biosensor of claim 1, wherein the capture molecule comprises a monoclonal antibody that specifically binds to a tuberculosis antigen.

8. The biosensor of claim 1, comprising a sample capture device configured to direct sample onto the sensing component.

9. The biosensor of claim 1, wherein the sensing component is removable.

10. The biosensor of claim 1, wherein the sensing component is configured for a single use.

11. The biosensor of claim 1, wherein the pH of the sensing component electrolytic gel is controlled by a bias dc voltage and configured for multiple use.

12. The biosensor of claim 1, wherein the electrolytic gel comprises agarose.

13. The biosensor of claim 1, wherein the biosensor comprises a housing which is sized to be handheld while in use.

14. The biosensor of claim 1, comprising a memory configured to store a set of impedance parameters, wherein the impedance parameters are specific to the biomolecule to be bound to the capture molecule.

15. The biosensor of claim 14, wherein the number of impedance parameters stored in the memory is less than 10.

16. The biosensor of claim 1, wherein the sensing component comprises a porous string-like medium immersed in the electrolytic gel.

17. The biosensor of claim 1, wherein the sensing component comprises a solid string-like material.

18. The biosensor of claim 8, wherein the sample capture device comprises a piezoelectric fan.

19. The biosensor of claim 1, wherein the SAM is a bifunctional molecule comprising both a thiol and a silane functional group.

20. A biosensor for detecting the presence and/or amount of a biomolecule in a sample, comprising:
    a) a housing;
    b) a sensing component, the sensing component comprising:
       (i) a string-like material contacting an electrolytic gel;
       (ii) colloidal gold nanoparticles linked to the string-like material, wherein the nanoparticles are each coated with a self-assembling monolayer ("SAM"), and wherein a portion of the SAM on the nanoparticles links the nanoparticles to the string-like material and another portion of the SAM on the nanoparticles links the nanoparticles to a capture molecule;

(iii) at least two electrodes in contact with the electrolytic gel and configured for impedance detection across the electrolytic gel;

c) an impedance measurement circuit coupled to the electrodes of the sensing component;

wherein the biosensor is configured to detect the presence and/or amount of the biomolecule in the sample in a non-liquid detection reaction.

21. The biosensor of claim 20, wherein the sensing component is configured to sense an air sample.

22. The biosensor of claim 20, wherein the capture molecule comprises an antibody.

23. The biosensor of claim 20, wherein the capture molecule comprises an antibody that specifically binds to a mold antigen.

24. The biosensor of claim 20, wherein the SAM is a bifunctional molecule comprising both a thiol and a silane functional group.

25. A method for detecting the presence and/or amount an airborne biomolecule of interest, the method comprising:

a) collecting an air sample that may contain the biomolecule of interest in the biosensor of claim 1;

b) contacting the air sample with the biosensor sensing component;

c) contacting the biomolecule of interest, if present, with the capture molecule of the sensing component;

d) identifying a change in impedance that is characteristic of the presence and/or amount of the biomolecule in contact with the capture molecule, thereby detecting the presence and/or amount of the biomolecule.

26. The method of claim 25, wherein the time elapsed between contacting the air sample with the sensing component and identifying a change in impedance characteristic of the presence and/or amount of the biomolecule is less than about 1 minute.

27. The method of claim 25, wherein the air sample is collected from the interior of a building, and the biomolecule of interest is a mold or is derived from a mold.

28. The method of claim 25, wherein the air sample is collected immediately above a water supply, and the biomolecule of interest comprises *Cryptosporidiidae cryptosporidium* or is derived from *Cryptosporidiidae cryptosporidium*.

29. The method of claim 25, wherein the air sample is collected outdoors.

30. The method of claim 25, wherein the capture molecule comprises a monoclonal antibody attached to a different antibody.

* * * * *